United States Patent [19]
Bolton et al.

[11] Patent Number: 5,889,034
[45] Date of Patent: Mar. 30, 1999

[54] ISOTHIAZOLONES

[75] Inventors: Gary Louis Bolton, Ann Arbor; John Michael Domagala, Canton; Edward Faith Elslager, Ann Arbor; Rocco Dean Gogliotti, Pinckney; Terri Stoeber Purchase, Ann Arbor; Joseph Peter Sanchez, Novi; Bharat Kalidas Trivedi, Farmington Hills, all of Mich.

[73] Assignee: Warner-Lambert Company, Morris Plains, N.J.

[21] Appl. No.: 40,777

[22] Filed: Mar. 18, 1998

Related U.S. Application Data

[62] Division of Ser. No. 757,716, Nov. 26, 1996, Pat. No. 5,733,921.

[51] Int. Cl.$^6$ ...................................................... A61K 31/41

[52] U.S. Cl. ........................... 514/373; 514/258; 514/301

[58] Field of Search ...................................... 514/258, 301, 514/373

[56] References Cited

U.S. PATENT DOCUMENTS 5,620,997   4/1997   Bolton ..................................... 514/373

*Primary Examiner*—Robert Gerstl
*Attorney, Agent, or Firm*—Charles W. Ashbrook

[57] ABSTRACT

Isothiazolones having the general structure

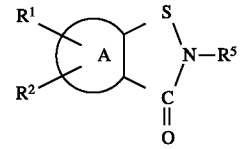

where A is a monocyclic or bicyclic ring which may contain up to 3 heteroatoms selected from O, S, and N; $R^1$ and $R^2$ are substituent groups such as alkyl, alkoxy, hydroxy, nitro, cyano, amino, and carboxy; and $R^5$ is alkyl, cycloalkyl, phenyl, and Het. The isothiazolones are useful as anti-retroviral agents, anti-inflammatory agents, and anti-atherosclerotic agents.

16 Claims, No Drawings

ISOTHIAZOLONES

This application is a divisional application of application Ser. No. 08/757,716, filed Nov. 26, 1996, now U.S. Pat. No. 5,733,921.

FIELD OF THE INVENTION

This invention provides isothiazolone derivatives which are useful as antiviral agents, anti-inflammatory agents, and anti-atherosclerotic agents. The invention is more particularly directed to bicyclic and polycyclic isothiazolones which are useful for treating retroviruses, including myeloblastosis associated virus, Rous sarcoma virus, human T-cell leukaemia virus, and HIV. The compounds also are effective for treating inflammation and atherosclerosis.

BACKGROUND OF THE INVENTION

Certain isothiazolones are known which have various pharmaceutical utilities, most notably antimicrobial activity. Okachi, et al., *J. Med. Chem.*, 1985; 28:1772–1779, describe several 1,2-benzisothiazolones which have marginal antibiotic activity and which were primarily utilized as intermediates in the synthesis of 2,2'-dithiobis (benzamide) derivatives. Carmellino, et al., *Eur. J. Med. Chem.*, 1994; 29:743–751, disclose a variety of 1,2-benzisothiazolones as antibacterial and antifungal agents. Miller, et al., U.S. Pat. No. 3,517,022, disclose 2-carbamoyl-1,2-benzisothiazolones which are said to be active against bacteria, fungi, and algae. Morley, in U.S. Pat. No. 3,012,039, describes 2-alkyl-1,2-benzisothiazolones which are useful as antibacterials and antifungals. Sherba, et al., U.S. Pat. No. 5,219,875, describe synergistic antimicrobial compositions comprising 2-unsubstituted 1,2-benzisothiazolin-3-one and iodopropargyl butylcarbamate. Laber, et al., U.S. Pat. No. 4,049,817, describe synergistic antimicrobial compositions containing a variety of 2-substituted and 2-unsubstituted benzisothiazolinones.

Grivos, U.S. Pat. No. 3,761,489, describes a series of substituted N-alkyl benzisothiazolinones which are said to be active against bacteria, fungi, and yeasts. Grivos, U.S. Pat. No. 3,661,974, describes the synthesis of various 2-substituted 1,2-benzisothiazolin-3-ones from 2-carbalkoxy-phenyl sulfonamides. The thiazolinones are said to be useful as antibacterials and antiseptics.

None of the references describing isothiazolones have disclosed that such compounds can be used to treat and prevent viral infections, inflammation, or atherosclerosis. We have now discovered that isothiazolones are potent anti-retroviral agents, and an object of this invention is to provide a method for preventing and treating viral diseases, including diseases caused by human T-cell leukaemia virus, Rous sarcoma virus, the myeloblastosis associated virus, various animal retroviruses, as well as HIV. A further object of the invention is to provide certain isothiazolones which are new compounds and which are especially useful for treating diseases caused by HIV. Still, a further object is to provide a method for treating inflammation and atherosclerosis by administering an isothiazolone.

SUMMARY OF THE INVENTION

This invention provides a method for preventing and treating retroviral infections, inflammation, and atherosclerosis comprising administering to a subject in need of treatment an effective amount of an isothiazolone. The invention is more particularly directed to a method of preventing and treating retroviral infections, inflammation, and atherosclerosis comprising administering a compound of Formula I

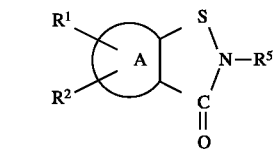

wherein:

A is a monocyclic ring having 5 or 6 ring atoms, or a bicyclic ring having from 9 to 12 ring atoms, the ring atoms being selected from carbon and optionally up to 3 heteroatoms selected from O, S, and N.

$R^1$ and $R^2$ independently are hydrogen, halo, $C_1$–$C_6$ alkyl, $C_3$–$C_6$ cycloalkyl, Het $(CR^6R^7)_m$—, phenyl-$(CR^6R^7)_m$—, O—$C_1$–$C_6$ alkyl, hydroxy, nitro, cyano, $NR^3R^4$, $NR^3COR^4$, $CO_2R^3$, $CONR^3R^4$, $S(O)_m R^3$, $SO_3H$, $S(O)_m NR^3R^4$, $COR^3$, or taken together are oxo (O=) or methylene dioxy (—O—$CH_2$—O—);

m is 0, 1, or 2;

$R^3$ and $R^4$ independently are hydrogen, $C_1$–$C_6$ alkyl, $C_3$–$C_6$ cycloalkyl, Het $(CR^6R^7)_m$—, or phenyl-$(CR^6R^7)_m$—;

$R^6$ and $R^7$ independently are hydrogen, $C_1$–$C_6$ alkyl, $CO_2R^3$, hydroxy, $CONR^3R^4$, or cyano;

$R^5$ is hydrogen, $C_1$–$C_6$ alkyl, $COC_1$–$C_6$ alkyl, $C_3$–$C_6$ cycloalkyl, phenyl-$(CR^6R^7)_m$—, Het$(CR^6R^7)_m$—; and wherein the foregoing alkyl, cycloalkyl, phenyl, and Het groups may optionally be substituted with from 1 to 3 groups selected from halo, hydroxy, nitro, $NR^3R^4$, $NR^3COR^4$, $CO_2R^3$, $CONR^3R^4$, $S(O)_m R^3$, $S(O)_m NR^3R^4$, and $COR^3$, where m, $R^3$, and $R^4$ are as defined above;

and the pharmaceutically acceptable salts and solvates thereof.

In a preferred embodiment, the isothiazolones utilized in the methods of this invention have Formula I above wherein A is a monocyclic ring having 6-ring atoms, one or two of which are heteroatoms selected from O, S, and N; ideally N.

In a further preferred embodiment, A is a monocyclic aromatic ring having 6-ring atoms, one or two of which are O, S, or N; ideally N. Especially preferred compounds within this group have the formulas

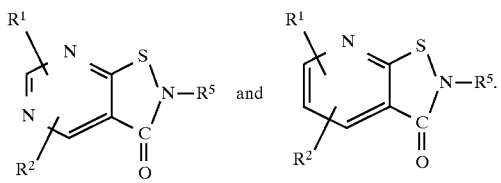

In another preferred embodiment, the isothiazolones utilized in the methods of the invention are benzisothiazolin-3-ones of Formula II

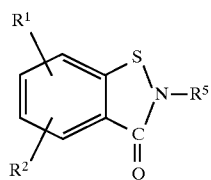

where

R$^1$ and R$^2$ independently are hydrogen, halo, C$_1$–C$_6$ alkyl or O—C$_1$–C$_6$ alkyl, and R$^5$ is C$_1$–C$_6$ alkyl, substituted C$_1$–C$_6$ alkyl, or unsubstituted or substituted phenyl-(CR$^6$R$^7$)$_m$—.

An especially preferred method for treating viral infections, inflammation, and atherosclerosis employs a compound having the Formula III

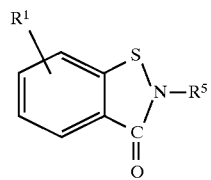

where R$^1$ is hydrogen, halo, alkyl or alkoxy, and R$^5$ is C$_1$–C$_6$ alkyl substituted with 1 or 2 CO$_2$R$^3$ groups, or phenyl substituted with S(O)$_m$NR$^3$R$^4$, where R$^3$ and R$^4$ are as defined above.

Another preferred method for treating viral infections, inflammation, and atherosclerosis employs a compound of Formula IVa and Formula IVb

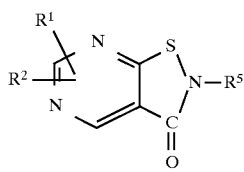

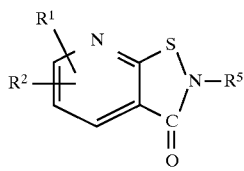

where R$^1$, R$^2$, and R$^5$ are as defined above.

The invention additionally provides a method for preventing and treating diseases caused by retroviruses, especially HIV.

Another embodiment of the invention are new chemical compounds characterized as isothiazolones of Formula V

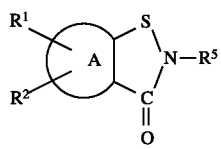

wherein

A is a monocyclic ring having 5 or 6 ring atoms, or a bicyclic ring having from 9 to 12 ring atoms, the ring atoms being selected from carbon and optionally up to 3 heteroatoms selected from O, S, and N;

R$^1$ and R$^2$ are as defined above; and

R$^5$ is as defined above, provided that when A is a monocyclic all-carbon ring, that R$^5$ is other than hydrogen, alkyl, hydroxy substituted alkyl, COC$_1$–C$_6$ alkyl, or unsubstituted or substituted phenyl-(CR$^6$R$^7$)$_m$—, when the substituent on the phenyl is alkyl, halo, alkoxy, or NR$^3$R$^4$, and the pharmaceutically acceptable salts and solvates thereof.

A preferred group of compounds provided by the invention have Formula VI

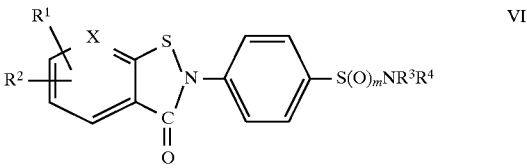

where X is CH or N, and R$^1$, R$^2$, R$^3$, and R$^4$ are as defined above.

A further preferred group of compounds have Formula VII

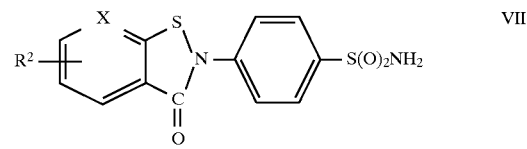

where X is CH or N, and R$^1$ is hydrogen, halo, C$_1$–C$_6$ alkyl, or O—C$_1$–C$_6$ alkyl.

Another preferred group of compounds have the Formula VIII

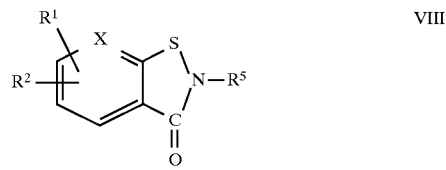

where X, R$^1$, and R$^2$ are as defined above, and R$^5$ is C$_1$–C$_6$ alkyl substituted with 1 or 2 CO$_2$R$^3$ groups, where R$^3$ is as defined above, and preferably is hydrogen or alkyl.

A particularly preferred group of compounds are those having a carboxy-substituted alkyl group for R$^5$, for example, compounds of the Formula IX

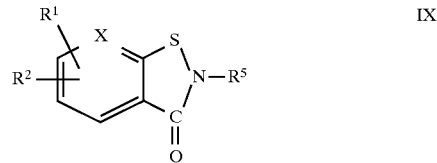

where R$^1$ and R$^2$ are as defined above, X is CH or N, and R$^5$ is C$_1$–C$_6$ alkyl substituted by 1 or 2 carboxy groups, and optionally substituted by hydroxy or amino. Especially preferred are the compounds wherein R$^5$ is a residue of an α-amino acid, where the amino group of the α-amino acid is part of the isothiazolone ring. Typical amino acid residues are those from glycine, alanine, valine, leucine, isoleucine, serine, threonine, lysine, δ-hydroxylysine, aspartic acid, glutamic acid, and the like.

Still another preferred group of compounds provided by the invention are pyrimidine derivatives having Formula X

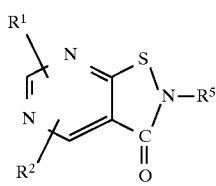

where $R^1$, $R^2$, and $R^5$ are as defined above.

DETAILED DESCRIPTION OF THE INVENTION

"$C_1$–$C_6$ alkyl" means a straight or branched aliphatic group having from 1 to 6 carbon atoms. Examples include methyl, ethyl, isobutyl, n-pentyl, and isohexyl.

The term "O—$C_1$–$C_6$ alkyl" means the foregoing alkyl radicals bonded through oxygen, examples of which include methoxy, ethoxy, isopropoxy, tert-butoxy, and the like. Typical "$C_3$–$C_6$ cycloalkyl" groups include cyclopropyl, cyclopentyl, cyclohexyl, and the like.

"Het" is a cyclic or bicyclic ring having from 4 to 10 atoms, from one to four of which are selected from O, S, or N. Het includes non-aromatic groups such as morpholino and pyrrlidino. Preferred Het groups are 5- or 6-membered mono-cyclic aromatic rings having 1 or 2 heteroatoms. Het includes bicyclic rings such as benzofuran, isothiazolone, indole, and the like. Typical groups represented by Het include

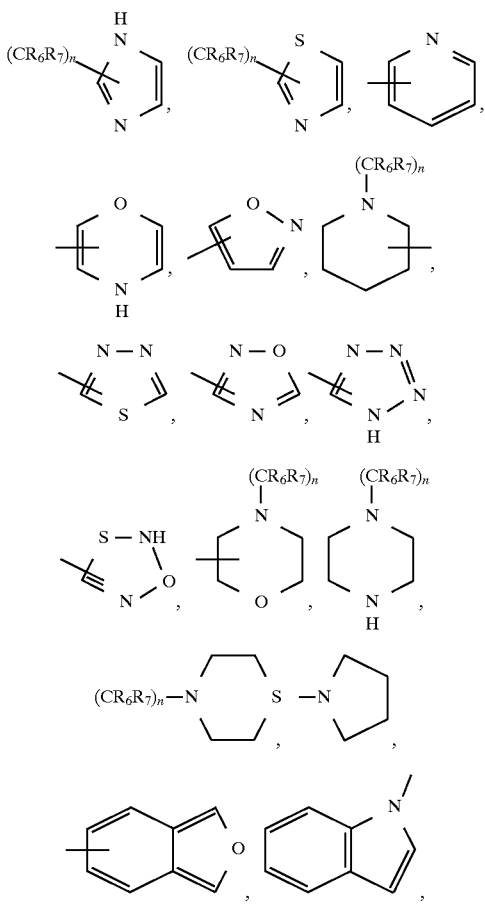

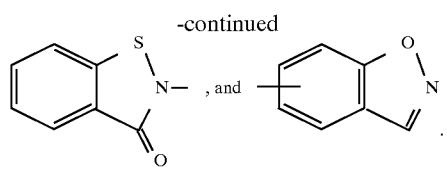

and the like. Other typically preferred Het groups include pyrimidine, pyridazine, pyrazine, oxazole, pyrazole, thiazole, and the like.

As noted above, the alkyl, cycloalkyl, phenyl and Het groups which are included in the definitions of $R^1$, $R^2$, $R^3$, $R^4$, and $R^5$ can be substituted with 1 to 3 groups selected from halo, hydroxy, $NR^3COR^4$, $CO_2R^3$, $NR^3R^4$, $CONR^3R^4$, $S(O)_mR^3$, $SO_3H$, $S(O)_mNR^3R^4$, and $COR^3$, where m, $R^3$, and $R^4$ are as defined above. Typical substituted alkyl groups thus include chloromethyl, 3-bromopropyl, trifluoromethyl, 4-hydroxyhexyl, 1-carboxy-2-methylbutyl, 3-methylthiobutyl, 4-methylsulfonylbutyl, dimethylaminomethyl, 2,3-dibromobutyl, 2-amino-3-chloro-4-carboxybutyl, 3-acetomidopropyl, 2-acetylethyl, 2-methoxycarbonyl-ethyl, 1,1-diacetylpropyl, and the like.

Preferred substituted alkyl groups are those having 1, 2, or 3 substituents selected from halo, hydroxy, and carboxy. Such preferred groups include 1-bromo-2-hydroxypropyl, 1,1-dimethyl-3-hydroxypropyl, 1-hydroxymethyl-2-fluoromethyl-3-carboxybutyl, 1-carboxy-2-methylbutyl, 1-carboxy-3-methylbutyl, 1,2,3-trihydroxypentyl, and the like.

Typical substituted cycloalkyl groups include 2-fluorocyclopropyl, 2,2-dibromocyclopropyl, 2 2-carboxycyclobutyl, 2-aminosulfonylcyclopentyl, 2-amino-3-carboxycyclopentyl, and 3-isopropylsulfinyl-cyclohexyl.

In the above formulas, $R^1$ and $R^2$ can be halo, which term includes fluoro, chloro, bromo, and iodo. $R^1$, $R^2$, and $R^5$ can include the group phenyl-$(CR^6R^7)_m$— in which the phenyl can be unsubstituted or substituted with halo, hydroxy, $NR^3R^4$, $NR^3COR^4$, $CO_2R^3$, $CONR^3R^4$, $S(O)_mR^3$, $S(O)_mNR^3R^4$, $SO_3H$, and $COR^3$. Typical $NR^3R^4$ substituents include amino, methylamino, dimethylamino, ethyl-isohexylamino, cyclopropylamino, 3-pyridylamino, N-methyl-2-thienylamino, benzylamino, and 3-chlorobenzylamino.

Typical substituents defined by $NR^3COR^4$ include cyclopropylcarbonylamino, N-isobutyl-N-cyclohexyl carbonylamino, acetamido, and the like. Typical groups defined by $CO_2R^3$ include the free carboxy acid when $R^3$ is hydrogen, and esters such as $C_1$–$C_6$ alkyl esters, benzyl esters, cyclobutyl esters, and the like. Amide substituents are defined by $CONR^3R^4$, and include carboxamide, N-methyl-carboxamide, and N,N-diethyl-carboxamide. Typical $S(O)_m R^3$ substituent groups include methylthio, ethylsulfinyl, cyclopropylsulfonyl, and the like. Sulfonamide substituents $S(O)_mNR^3R^4$ include N-methylsulfonamide, N,N-dimethylsulfonamide, and the like. Typical phenyl-$(CR^6R^7)_m$— groups substituted with the foregoing substituent groups thus include:

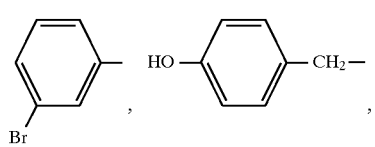

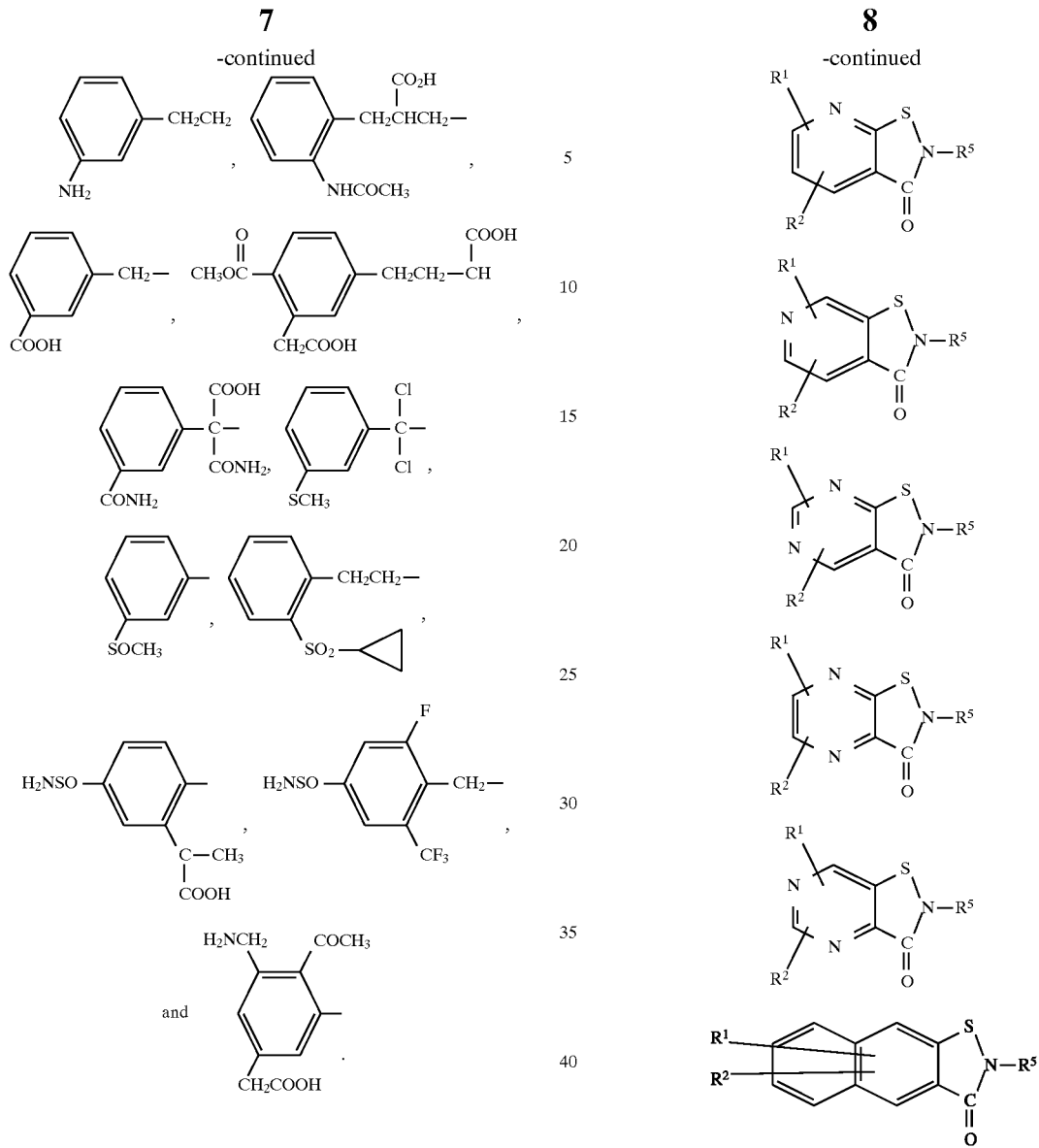
The compounds of the invention can be bicyclic or tricyclic, for example, when A in Formula I is a monocyclic ring or a bicyclic ring, respectively. The compounds can have from 1 to 3 heteroatoms selected from O, S, and N as part of the A ring system. Typical bicyclic and tricyclic isothiazolones contemplated herein include:
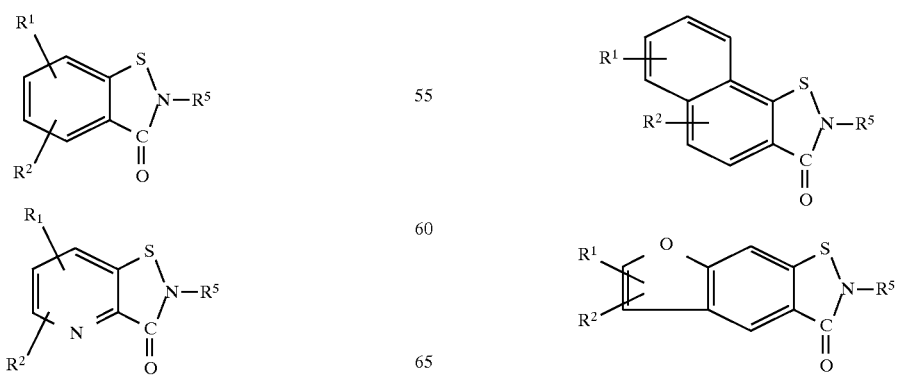

-continued

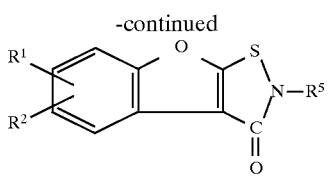
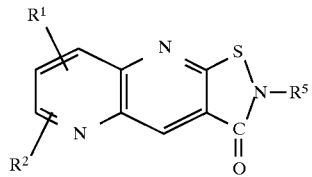
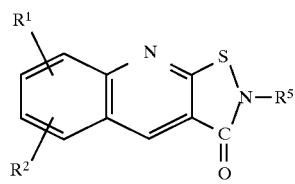
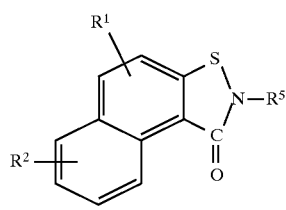
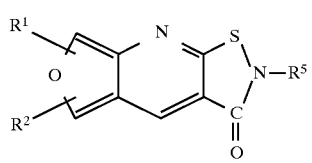
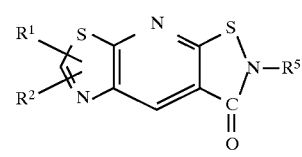
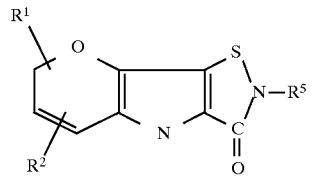
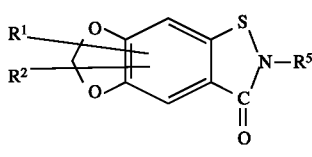
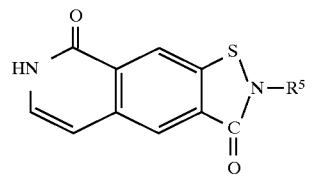

-continued

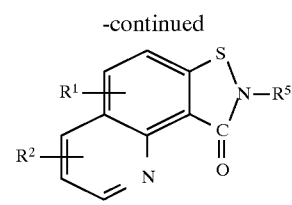
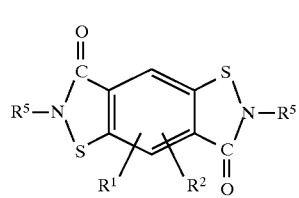
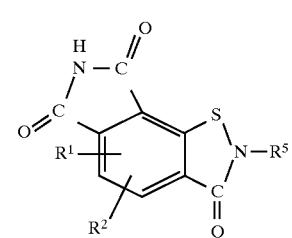

Typical substituted $Het(CR^6R^7)_m$— include:

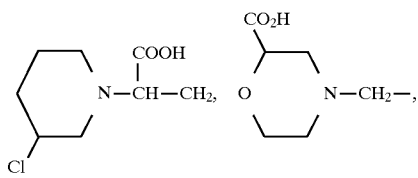
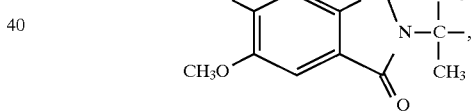
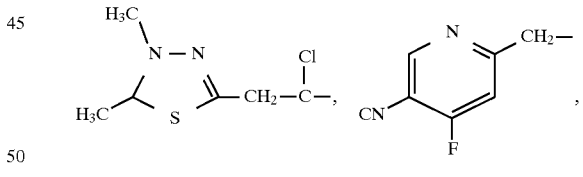

The compounds to be utilized to treat and prevent retroviral infections, inflammation, and atherosclerosis according to this invention can be prepared by any of several synthetic processes utilizing common methodology. For example, an O-halosulfenylbenzoyl halide can be reacted with an amine according to the following scheme, which is the general method of Fisher and Hurni, *Arzneithmittel Forsch.*, 1964; 14:1301:

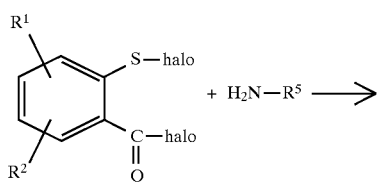

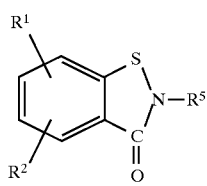

where $R^1$, $R^2$, and $R^5$ are as defined above, and "halo" includes chloro, bromo, iodo, and the like. Typically, the amine and halosulfenylbenzoyl halide are employed in approximately equimolar quantities; however, an excess of the amine can be utilized if desired. The reaction generally is substantially complete within about 1 to 8 hours when carried out in a mutual solvent such as toluene, ethylene dichloride, or methylene chloride at a temperature of about 0° C. to 45° C. Acid scavengers, such as triethylamine, can be utilized if desired. The product isothiazolone is readily isolated by removing the reaction solvent, and further purification can be accomplished by crystallization or chromatography, if desired. The process is equally applicable to all A systems contemplated.

An alternative method of synthesis comprises reacting a 2-unsubstituted isothiazolone with a compound $R_5L$, where L is a leaving group such as halo. This reaction is depicted as follows:

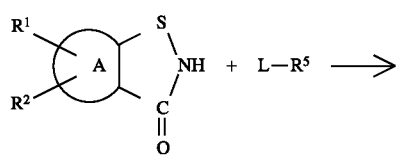

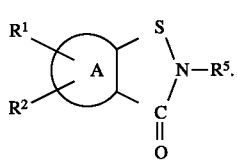

Specific reaction conditions, such as choice of solvents, temperature, molar ratios, acid scavengers, and the like, are similar to the process described above, and are well within the skill of the art.

A preferred method for preparing the isothiazolones comprises disproportionate of a 2,2'-dithiobis aryl amide by reaction with an oxidizing agent such as chlorine or bromine according to the following scheme:

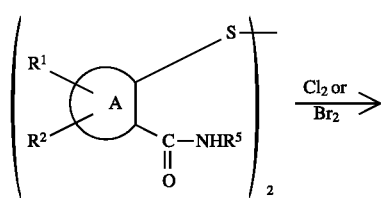

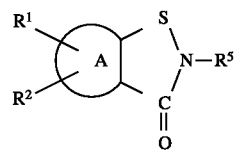

where $R^1$, $R^2$, and $R^5$ are as defined above. This disproportionate reaction requires starting with a 2,2'-dithio bisaryl amide, and these are readily prepared from 2,2'-dithio bisaryl carboxylic acids by reacting the acid with a chlorinating agent such as oxalyl chloride or thionyl chloride to produce the corresponding acid chloride, and then reacting the acid chloride with an amine $R_5NH_2$. A typical synthesis follows the following scheme:

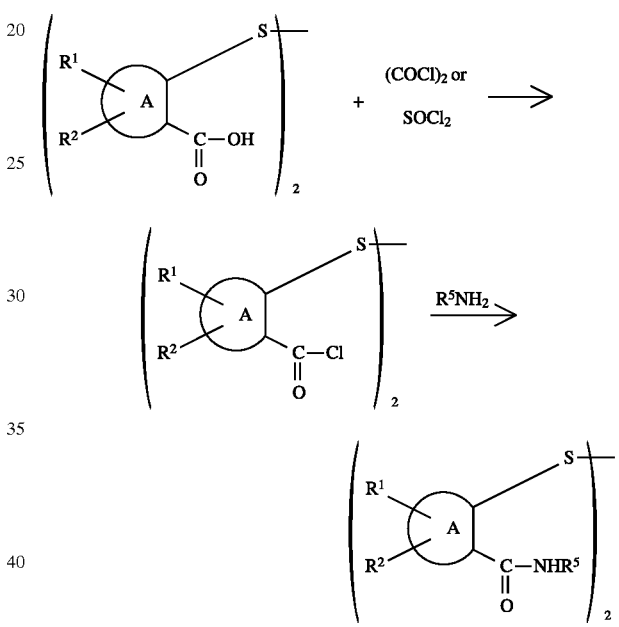

The 2,2'-dithio-bisaryl carboxylic acids required for the above synthesis are well known in the art or are readily prepared by routine methods. Typical aryl carboxylic acids commonly used include those of the following general structures:

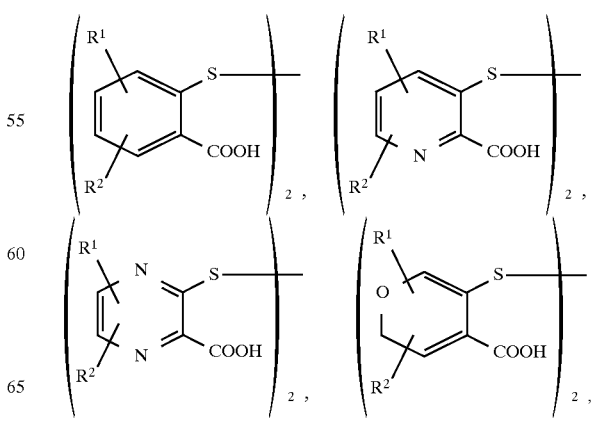

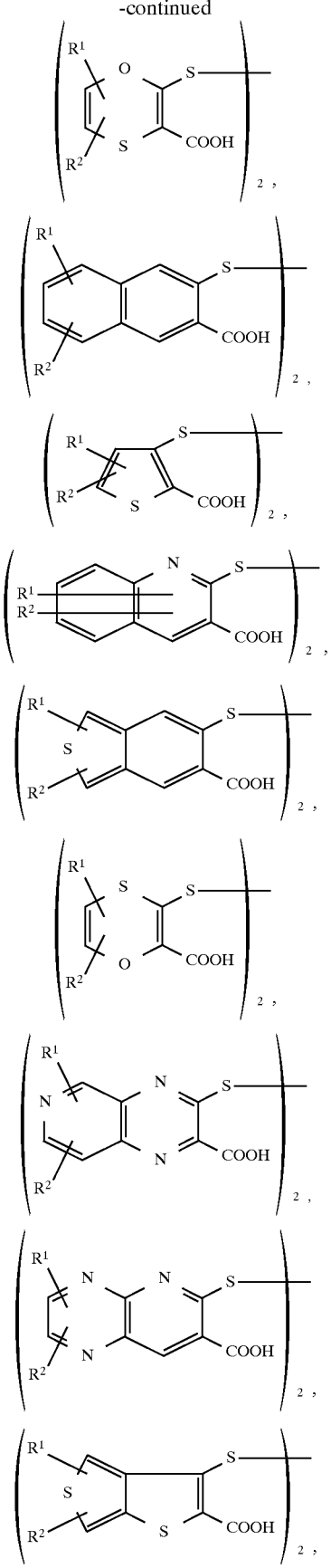

The 2,2'-dithio-bisaryl carboxylic acids are readily converted to the corresponding acid chlorides by reaction with a chlorinating agent such as thionyl chloride or oxalyl chloride. The reaction can be carried out neat or in an unreactive organic solvent such as dichloromethane, tetrahydrofuran, diethyl ether, dimethylformamide, or the like. The reaction generally is complete within about 1 to about 8 hours when carried out at a temperature of about 0° C. to about 100° C. The product acid chlorides are readily isolated simply by removing the reaction solvent and excess chlorinating agent, for example by evaporation under reduced pressure.

The 2,2'-dithio-bisaryl carboxylic acid chlorides are next converted to 2,2'-dithio-bisarylamides by reaction with a primary amine of the formula $R^5NH_2$. Typical primary amines commonly employed include alkyl amines and substituted alkyl amines such as methylamine, leucine, isoleucine, serine, threonine, lysine, asparagine, and the like. Aniline and substituted anilines can also be employed, such as 4-hydroxyaniline, 3-aminoaniline, 3-methylthioaniline, 4-dimethylsulfamoylaniline, and the like. The amine and acid chloride generally are mixed in approximately equimolar quantities in a mutual solvent such as acetone, dichloromethane, tetrahydrofuran, methanol, and the like. Acid scavengers such as pyridine, triethylamine, N-methylmorpholine, and the like, can be utilized if desired. The reaction generally is complete within about 1 to about 18 hours when carried out at a temperature of about 0° C. to about 100° C. The 2,2'-dithio-bisaryl amides that are formed are easily isolated by simply removing the reaction solvents and any excess reactants by evaporation under reduced pressure, and further purification generally is not required.

The 2,2'-dithiobisaryl carboxamides can be converted to the isothiazolones of the invention in either of two ways. The carboxamides readily react with oxidizing agents such as bromine or chlorine to effect cyclization to the corresponding isothiazolones. The oxidation generally is carried out by mixing an excess of chlorine or bromine with the carboxamide in a suitable solvent such as a halogenated hydrocarbon, dimethylsulfoxide, dimethylformamide, or the like, typically at a reduced temperature of about 0° C. to about 5° C. The product isothiazolone is generally solid at room temperature and normally precipitates from the reaction mixture. It can be recovered by filtration, and further purified, if desired, by routine methods such as washing, for instance with aqueous sodium bicarbonate or the like, and crystallized from common solvents such as acetone, ethanol, ethyl acetate, and the like.

An alternative method for making the isothiazolones from the 2,2'-dithiobis aryl carboxamides comprises first converting the dithiobis intermediate to the corresponding aryl thiol carboxamide derivative, and then cyclizing the thiol and carboxamide to form the final product. This scheme is depicted below:

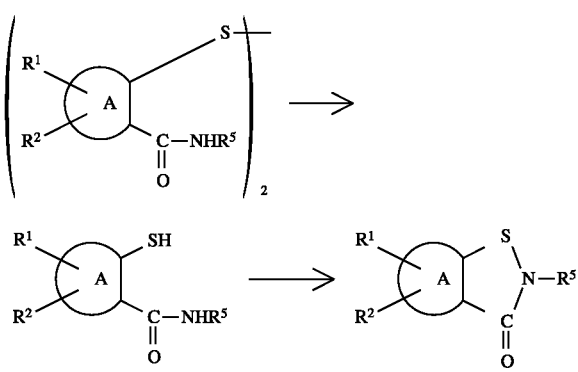

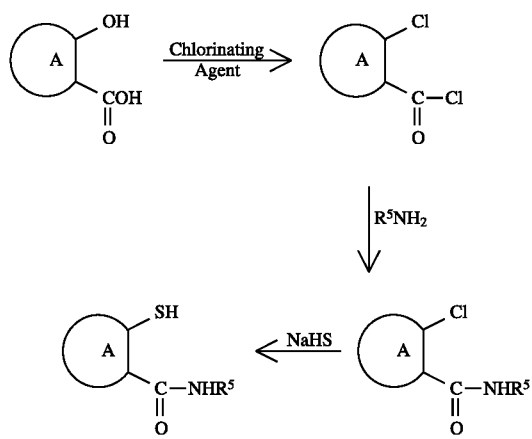

The dithiobis intermediates are reacted with a reducing agent such as dithiothreitol (DTT) in a mutual solvent such as dimethylformamide, dimethylsulfoxide, dioxane, and the like. The reduction typically is carried out at a temperature of about 10° C. to about 30° C., and normally is complete within about 0.5 to about 4 hours. The product aryl thiol carboxamide generally is not isolated, other than removing any reaction solvent by evaporation.

The aryl thiol carboxamide can also be prepared from readily available 2-hydroxycarboxylic acids according to the following scheme:

In this process, a 2-hydroxycarboxylic acid is reacted with an excess of a common chlorinating agent such as thionyl chloride or phosphorus pentachloride in an unreactive organic solvent such as ethylene dichloride, chloroform, ethyl chloride, toluene, or the like, typically at a temperature of about 25° C. to about 60° C. The product, a 2-chloro acid chloride derivative, generally is isolated by simply removing the reaction solvent and excess chlorinating agent, for instance by evaporation under reduced pressure. The chloro acid chloride is then reacted with a primary amine, $R^5NH_2$, in an unreactive organic solvent such as chloroform, methylene chloride, ethyl chloride, or the like. Typical primary amines commonly employed include natural α-amino acids such as glycine, leucine, isoleucine, lysine, aspartic acid, and the like. Tertiary and aromatic amines such as triethylamine, pyridine, or N-methyl morpholine can be added to act as acid scavenger for the hydrochloric acid that is formed during the reaction. The chloro carboxamide that is produced is readily isolated by removing the reaction solvent, and further purification can be accomplished by routine methods such as crystallization, chromatography, and the like. The chloro carboxamide is next reacted with sodium hydrogen sulfide in a polar solvent such as methanol, ethanol, isopropanol, or the like to give the corresponding 2-thiol carboxamide derivative.

The aryl thiol carboxamide is next reacted with an agent to effect cyclization. Typical agents routinely utilized include chlorocarbonyl sulfenyl chloride, iodine, bromine, and the like. The cyclization is accomplished by mixing equimolar quantities of the thiol carboxamide and cyclizing agent in an unreactive organic solvent such as tetrahydrofuran or the like, and stirring the mixture for about 0.5 to about 18 hours at a temperature of about 0° C. to about 30° C. The product isothiozolone typically precipitates as it is formed, and is readily isolated by filtration, and further purified, if desired, by crystallization, chromatography, and the like.

Many of the compounds embraced by Formula I can have functional substituent groups (e.g., $R^1$ and $R^2$) which may need to be derivatized in order to avoid unwanted side reactions during synthesis. Such functional substituent groups include, for example, hydroxy groups, amino groups, especially primary and secondary amino groups, and carboxylic acid groups. For example, hydroxy groups, in order to prevent unwanted side reactions, generally need to be converted to protected hydroxy groups such as ethers or esters during chemical reactions at other sites in the molecule. The hydroxy protecting group is subsequently removed to provide the free hydroxy group. Amino groups and carboxylic acid groups are similarly derivatized to protect them against unwanted side reactions. Carboxy groups generally are converted to esters such as tert.-butyl ester, benzyl or p-nitrobenzyl ester, and the like. Amino groups typically are acylated, for example with acetyl chloride or the like, or silylated with trimethylsilyl or t-butyldimethylsilyl groups. Typical protecting groups, and methods for attaching and cleaving them, are described fully by Greene and Wuts in *Protective Groups in Organic Synthesis*, John Wiley and Sons, New York, (2nd Ed; 1991), and McOmie, *Protective Groups in Organic Chemistry*, Plenum Press, New York, 1973.

Many of the isothiazolones of Formula I are capable of forming pharmaceutically acceptable salts, including acid addition salts and base salts, as well as solvates, such as hydrates and alcoholates. All of these pharmaceutical forms are contemplated by this invention and are included herein. Acid addition salts are readily formed when a Formula I compound contains amino substituent groups, or nitrogen atoms are present in the A ring system. Base salts can be formed when carboxylic acid substituent groups are present, for example, when $R^5$ is a carboxy substituted alkyl such as carboxymethyl or the like.

Pharmaceutically acceptable acid addition salts of the compounds of Formula I include salts derived from inorganic acids such as hydrochloric, nitric, phosphoric, sulfuric, hydrobromic, hydriodic, phosphoric, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S.M., et al., "Pharmaceutical Salts," *J. of Pharmaceutical Science,* 1977; 66:1–19.

The acid addition salts of basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S.M., et al., "Pharmaceutical Salts," *J. of Pharmaceutical Science,* 1977; 66:1–19.

The base addition salts of acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Many of the isothiazolones of Formula I contain one or more asymmetric carbon atoms, and as such, can exist in optically active forms. For example, a preferred group of compounds are those wherein $R^5$ is a residue of an α-amino acid such as alanine, valine, leucine, threonine, and the like. Such groups have one or more asymmetric centers. The racemates can be separated into their respective enantiomers by routine methodology, including fractional crystallization, high performance liquid chromatograph, asymmetric synthesis, and the like. The racemates and individual enantiomers are contemplated equally by this invention.

While the forms of the invention herein constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

The following detailed examples illustrate specific embodiments of the invention. The examples are intended to be a general illustration of how to make and use the invention, and are not intended to be limiting in any respect.

Unless otherwise stated, all reagents were obtained from commercial sources. Many of the aryl thiol carboxamides which are utilized as starting materials are known or are available by the methods described, for example, by Bell, *J. Am. Chem. Soc.,* 1942:2905, Carmellino, et al., *Eur. J. Med. Chem.,* 1994;29:743–751, Bennett, et al., *Organic Prep. and Proced. Int.,* 1974;6(6):287–293 and Vitali, et al., *Il Farmaco Ed. Sc.,* 1968;23:468–476. These references are incorporated herein by reference for their teaching of synthetic methods for aryl thio carboxamides.

PREPARATION 1

2,2'-Dithiobisbenzoyl chloride

A mixture of 2,2'-dithiobisbenzoic acid (25 g, 81.6 mmol) in 350 mL of thionyl chloride was heated at reflux for 18 hours. The resulting solution was cooled and excess thionyl chloride was removed in vacuo. The crude solid was slurried in hexane and the title compound was recovered by filtration to yield 21.2 g mp 150°–151° C. This compound was used without further purification.

PREPARATION 2

2,2'-Dithiobis[5-fluorobenzoyl chloride]

A mixture of 2,2'-dithiobis[5-fluorobenzoic acid] (5.0 g, 14.6 mmol) and thionyl chloride (40 mL) was reacted according to the procedure described above to yield 4.9 g of 2,2'-dithiobis[5-fluorobenzoyl chloride]. This compound was used without further purification.

PREPARATION 3

2,2'-Dithiobis[5-methoxybenzoyl chloride]

A mixture of 2,2'-dithiobis[5-methoxybenzoic acid] (0.8 g, 2.0 mmol) and thionyl chloride (10 mL) was reacted according to the procedure described above to yield 0.8 g of 2,2'-dithiobis[5-methoxybenzoyl chloride]. This compound was used without further purification.

PREPARATION 4

2,2'-Dithiobis[5-methylbenzoic acid]

A mixture of 2,2'-dithiobis[5-methylbenzoic acid] (0.6 g, 1.8 mmol) and thionyl chloride (10 ml) was reacted according to the procedure described above to yield 0.3 g of 2,2'-dithiobis[5-methylbenzoyl chloride]. The compound was used without further purification.

PREPARATION 5

2,2'-Dithiobis[4-fluorobenzoyl chloride]

A mixture of 2,2'-dithiobis[4-fluorobenzoic acid] (5.0 g, 14.6 mmol) and thionyl chloride was reacted according to the procedure described above to yield 4.1 g of 2,2'-dithiobis[4-fluorobenzoyl chloride]. The compound was used without further purification.

PREPARATION 6

2,2'-Dithiobis[4-methoxybenzoyl chloride]

A mixture of 2,2'-dithiobis[4-methoxybenzoic acid] (2.2 g, 6.6 mmol) and thionyl chloride (20 mL) was reacted according to the procedure described above to yield 2.1 g of 2,2'-dithiobis[4-methoxybenzoyl chloride]. No further purification was required.

PREPARATION 7

2,2'-Dithiobis [4-methylbenzovl chloride]

A mixture of 2,2'-dithiobis[4-methylbenzoic acid] (3.8 g, 11.9 mmol) and thionyl chloride (50 mL) was reacted according to the procedure described above to yield 3.6 g of 2,2'-dithiobis[4-methylbenzoyl chloride]. The compound was used without further purification.

PREPARATION 8

2,2'-Dithiobis[3-pyridinecarbonyl chloride]

A mixture of 2,2'dithiobis[3-pyridinecarboxylic acid (1.5 g, 4.8 mmol) and thionyl chloride (20 mL) was reacted according to the procedure described above to yield 1.3 g of 2,2'-dithiobis[3-pyridinecarbonyl chloride]. The compound was used without further purification.

PREPARATION 9

2,2'-Dithiobis[4'-sulfamoylbenzanilide] (general method)

A solution of 2,2'-dithiobisbenzoyl chloride (5.0 g, 14.0 mmol) from Preparation 1 in 50 mL of dichloromethane was added dropwise to a solution of 4-(aminosulfonyl)-aniline (6.2 g, 36.0 mmol) in 125 mL pyridine cooled to 0° C. The mixture was stirred for 18 hours, and the resulting solid was removed by filtration, washed with 1N HCl, water, and dried in vacuo to yield 7.6 g of crude product. This crude material (6.5 g) was suspended in 50 mL dimethylformamide/60 mL ethanol, filtered, and precipitated from the filtered solution with the addition of 10 mL 4% aqueous $NaHCO_3$. The product was collected by filtration, washed with ethanol and water to yield 4.3 g of the title compound, mp 311°–312° C.

PREPARATION 10

2,2'-Dithiobis[4'-sulfamoyl(4-methoxybenzanilide)]

This compound was prepared according to the general method described in Preparation 9 using 2,2'-dithiobis[4-methoxybenzoyl chloride] (1.1 g, 2.7 mmol) in dichloromethane (10 mL) and 4-(aminosulfonyl)-aniline (1.1 g, 6.8 mmol) in pyridine (15 mL). The crude product was recrystallized from dimethylformamide, ethanol, and water to yield 0.8 g of the title compound.

PREPARATION 11

2,2'-Dithiobis [4'-sulfamoyl(4-methylbenzanilide)]

This compound was prepared according to the general procedure described in Preparation 9 using 2,2'-dithiobis [4-methylbenzoyl chloride] (2.0 g, 5.5 mmol) in dichloromethane (20 mL) and 4-(aminosulfonyl)-aniline (3.4 g, 19.9 mmol) in pyridine (40 mL). The crude product was recrystallized from dimethylformamide, ethanol, and water to afford 2.1 g of the title compound.

PREPARATION 12

2,2'-Dithiobis [4'-sulfamoyl(4-fluorobenzanilide)]

This compound was prepared according to the general procedure described in Preparation 9 using 2,2'-dithiobis [4-fluorobenzoyl chloride] (2.0 g, 5.2 mmol) in dichloromethane (20 mL) and 4-(aminosulfonyl)-aniline (2.2 g, 13.0 mmol) in pyridine (30 mL). The crude product was recrystallized from dimethylformamide, ethanol, and water to yield 2.6 g of the title compound.

PREPARATION 13

2,2'-Dithiobis [4'-sulfamoyl (5-methylbenzanilide)]

This compound was prepared according to the general method of Preparation 9 using 2,2'-dithiobis [5-methylbenzoyl chloride] (2.0 g, 5.3 mmol) in dichloromethane (20 mL) and 4-(aminosulfonyl)-aniline (2.3 g, 13.3 mmol) in pyridine (30 mL). The crude product was recrystallized from dimethylformamide, ethanol, and water to yield 1.8 g of the title compound.

PREPARATION 14

[S-(R*,R*)]-2-[2-[2-(1-tert-Butoxycarbonyl-3-methyl-butylcarbamoyl)-5-methoxy-phenyldisulfanyl]-4-methoxy-benzoylamino]-4-methyl-pentanoic acid tert-butyl ester (general method)

A solution of 2,2'-dithiobis [4-methoxybenzoyl chloride] (1.1 g, 2.7 mmol) from Preparation 9 in 10 mL of dichloromethane was added dropwise to a solution of L-leucine, t-butyl ester, monohydrochloride (1.5 g, 6.8 mmol) and N-methyl morpholine (1.6 mL, 14.0 mmol) in 25 mL dichloromethane cooled to 0° C. to 5° C. The resulting solution was stirred for 18 hours, and then warmed to ambient temperature (25° C.). The mixture was extracted with 0.5N HCl, water, 8% aqueous $NaHCO^3$, and brine. The organic layer was dried with $MgSO_4$, filtered, and concentrated in vacuo. The crude product was recrystallized from ethyl acetate to yield 1.2 g of the title compound.

PREPARATION 15

[S-(R R*)-2-[2-[2-(1-tert-Butoxycarbonyl-3-methyl-butylcarbamoyl)-4-fluoro-phenyldisulfanyl]-5-fluorobenzoylamino]-4-methyl-pentanoic acid tert-butyl ester This compound was prepared according to the general method of Preparation 14 using 2,2'-dithiobis [5-fluorobenzoyl chloride] (2.0 g, 5.2 mmol) in 20 mL dichloromethane, L-leucine, t-butyl ester, monohydrochloride (2.5 g, 11.4 mmol), and N-methyl morpholine (1.4 mL, 12.5 mmol) in 30 mL dichloromethane. The crude product was recrystallized from ethyl acetate to yield 1.8 g of the title compound.

PREPARATION 16

[S-(R*,R*)]-2-[2-[2-(1-tert-Butoxycarbonyl-3-methyl-butylcarbamoyl)-5-methyl-phenyldisulfanyl]-4-methylbenzoylamino]-4-methyl-pentanoic acid tert-butyl ester This compound was prepared according to the general method described in Preparation 14 using 2,2'-dithiobis [4-methylbenzoyl chloride] (1.8 g, 7.8 mmol) in 20 mL dichloromethane, L-leucine, t-butyl ester, monohydrochloride (4.0 g, 17.9 mmol), and N-methyl morpholine (4.6 mL, 41 mmol) in 60 mL dichloromethane. The crude product was recrystallized from ethyl acetate to yield 1.9 g of the title compound.

PREPARATION 17

[S-(R*,R*)]-2-[[2-[3-(1-tert-Butoxycarbonyl-3-methyl-butylcarbamoyl)-pyridin-2-yldisulfanyl]-pyridine-3-carbonyl]-amino]-4-methyl-pentanoic acid tert-butyl ester This compound was prepared according to the general method described in Preparation 14 using 2,2'-dithiobis [3-pyridinecarbonyl chloride] (0.8 g, 2.1 mmol) in 10 mL dichloromethane and L-leucine, t-butyl ester, monohydrochloride (1.5 g, 5.7 mmol) in 20 mL pyridine. The crude product was recrystallized from ethyl acetate to yield 1.9 g of the title compound.

PREPARATION 18

[S-(R*,R*)]-2-[2-[2-(1-Carboxy-2-methylbutylcarbamoyl) phenyldisulfanyl]-benzoylamino]-3-methylpentanoic acid tert-butyl ester A solution of 10.0 g (53.2 mmol) of L-isoleucine t-butyl ester in 100 mL of dichloromethane was mixed with 5.6 g (55.0 mmol) of N-methylmorpholine. The resulting solution was cooled to 0° C. and reacted by rapid dropwise addition of a solution of 8.3 g (24.2 mmol) of 2,2'-dithiobisbenzoyl chloride (from Preparation 1) in 100 mL of dichloromethane, keeping the temperature below 0° C. The mixture was stirred at 0° C. for 1 hour and then stirred at room temperature for 18 hours. The solid which had formed was removed by filtration, washed with water, and dried in vacuo to give 6.5 g of the title compound. The filtrate was washed with water, 0.5M hydrochloric acid, water, dried (MgSO$_4$), filtered, and evaporated in vacuo to give an additional 6.9 g of the title compound having comparable purity.

PREPARATION 19

[S-(R*,R*)]-2-[2-[2-(1-Carboxy-2-methylbutylcarbamoyl)-phenyldisulfanylbenzoylamino]-3-methylpentanoic acid A solution of 13.2 g (20.5 mmol) of the tert-butyl ester (from Preparation 18) in 50 mL of trifluoroacetic acid was stirred at room temperature for 18 hours. The solvent was removed in vacuo, and the residue was dissolved in 50 mL of dichloromethane. The dichloromethane was removed in vacuo, and the residue was triturated with 150 mL of diethyl ether/pentane (2:1 v/v), and the resulting solid was removed by filtration. After washing with 50 mL of diethyl ether/pentane (2:1) and then with pentane, the solid was dried in vacuo and identified as 9.9 g of the title compound, mp 211°–213° C.

PREPARATION 20

[S-(R*,R*)[-2-[2-[2-(1-Carboxy-3-methyl-butylcarbamoyl)-5-methoxy-phenyldisulfanyl]-4-methoxybenzoylaminol-4-methyl-pentanoic acid (general method)

A solution of [S-(R*,R*)-2[2-[2-(1-tert-butoxycarbonyl-3-methyl-butylcarbamoyl)-5-methoxyphenyldisulfanyl]-4-methoxybenzoylamino]-4-methyl-pentanoic acid tert-butyl ester (1.2 g, 1.7 mmol) and anisole (1 mL) in 10 mL dichloromethane, cooled to about 0° C., was treated dropwise with 10 mL of trifluoroacetic acid. The mixture was allowed to warm to ambient temperature. After 4 hours, 5 mL toluene was added, and the solvents were removed in vacuo. The crude product was recrystallized from methanol/water to yield 0.7 g of the title compound.

PREPARATION 21

[S-(R*,R*)]-2-[2-[2-(1-Carboxy-3-methyl-butylcarbamoyl)-4-fluorophenyldisulfanyl]-5-flourobenzoylaminol-4-methyl-pentanoic acid The general method of Preparation 20 was followed using [S-(R*,R*)]-2-[2-[[2-(1-tert-butoxycarbonyl-3-methyl-butylcarbamoyl)-4-fluorophenyldisulfanyl]-5-fluorobenzoylamino)-4-methyl pentanoic acid tert-butyl ester (1.8 g, 2.6 mmol) in 20 mL dichloromethane, anisole (2 mL), and 20 mL trifluoroacetic acid. The crude product was recrystallized from methanol/water to afford 0.9 g of the title compound.

PREPARATION 22

[S-(R*,R*)]-2-[2-(1-Carboxy-3-methyl-butylcarbamoyl)-5-methylphenyldisulfanyl]-4-methylbenzoylamino]-4-methyl-pentanoic acid The general method of Preparation 20 was followed using [S-(R*,R*)]-2-[2-[2-(1-tert-butoxycarbonyl-3-methyl-butylcarbamoyl)-5-methyl-phenyldisulfanyl]-4-methyl-benzoylamino]-4-methyl-pentanoic acid tert-butyl ester (1.9 g, 2.8 mmol) in 20 mL dichloromethane, anisole (2.0 mL), and 10 mL trifluoroacetic acid. The crude product was recrystallized from methanol/water to yield 1.1.g of the title compound.

PREPARATION 23

[{S-(R*,R*)]-2-[[2-[3-(1-Carboxy-3-methyl-butylcarbamoyl)-pyridin-2-yl-disulfanyl]-pyridine-3-carbonyl]-amino)-4-methyl-pentanoic acid The general method of Preparation 20 was followed using [S-(R*,R*)]-2-([2-[3-(1-tert-butoxycarbonyl-3-methyl-butylcarbamoyl)-pyridin-2-yldisulfanyl]-pyridine-3-carbonyl]-amino)-4-methyl-pentanoic acid tert-butyl ester (1.9 g, 2.9 mmol) in 20 mL dichloromethane, anisole (1.5 mL), and 10 mL trifluoroacetic acid. The crude product was recrystallized from methanol/water to yield 1.2 g of the title compound.

PREPARATION 24

2-Chloro-5-nitrobenzamide

A mixture of 2-chloro-5-nitrobenzoic acid (15.0 g, 74.0 mmol) and 200 mL of dichloromethane was reacted with oxalyl chloride (16.2 mL, 186.0 mmol) and a catalytic amount of dimethylformamide. The mixture was stirred at 25° C. for 3 hours. The solvent was removed in vacuo, and the residue was redissolved in 200 mL of dichloromethane. The solution was cooled to 0° C., and ammonia was bubbled through the cold solution for 5 minutes, whereupon the product precipitated to form solution. The product was collected by filtration to yield 6.8 g, mp 174°–175° C.

PREPARATION 25

2,2'-Dithiobis(5-nitrobenzamide)

To a refluxing solution of 2-chloro-5-nitrobenzamide (6.8 g, 33.0 mmnol) from Preparation 24 in 90 mL of ethanol was added portion-wise sodium sulfide hydrate, Na$_2$S(9H$_2$O) (2.6 g, 20.5 mmol) and sulfur (0.7 g, 20.5 nmmol). The mixture was heated at reflux for 1 hour, then cooled to room temperature, whereupon a solid formed. The solid was collected by filtration to yield 2.6 g of the title compound, mp 266°–269° C.

PREPARATION 26

2,2'-Dithiobis(5-aminobenzamide)

2,2'-Dithiobis(5-nitrobenzamide) (2.6 g, 7.0 mmol) was added portion-wise to a refluxing slurry of reduced iron (8.7 g) in 65 mL of water containing 0.1 mL of acetic acid. The resulting slurry was heated at reflux for 2.0 hours, then cooled to room temperature. The slurry was made strongly basic (pH 11) by the addition of 14 mL of 1N NaOH. The alkaline mixture was filtered, and acetic acid was added to the solution to adjust the pH to 7.0. While bubbling oxygen into the solution, a pH=6–7 was maintained with the addition of acetic acid. A solid gradually formed as the pH begins to stabilize. The product (1.1 g) was recovered by filtration, mp 188°–190° C.

PREPARATION 27

2,2'-Dithiobis(5-acetylamino)benzamide 2,2'-Dithiobis(5-aminobenzamide) (1.1 g, 3.4 mmol) was dissolved in 6 mL of glacial acetic acid on a steam bath and reacted with acetic anhydride (0.7 mL, 7.2 mmol). Upon cooling, the product precipitated from solution. An additional 4 mL of glacial acetic acid and 0.1 mL of acetic anhydride was added, and the mixture was heated at reflux for 30 minutes, and then cooled to room temperature. The crude product was recovered by filtration and recrystallized from dimethylformamide/dimethyl sulfoxide/water to yield 0.8 g of the title product, mp 301°–303° C.

PREPARATION 28

2,2'-Dithiobis [N-[4-[(acetylamino)sulfonyl]phenyl] benzamide]

The compound was prepared according to the general method of Preparation 9 using 2,2'-dithiobisbenzoyl chloride (3.0 g, 8.0 mmol) in 30 mL of dichloromethane and 4-[(acetylamino)sulfonyl]aniline (5.6 g, 26.0 mmol) in 100 mL of pyridine. The crude product was purified on a silica gel column using chloroform/methanol (1:1 v/v) as the mobile phase. The pure fractions were pooled, concentrated in vacuo, and the solid was crystallized from ethanol/water (1:1 v/v) to yield 0.5 g of the title compound, mp 180°–182° C.

PREPARATION 29

2-Mercapto-N-(4-sulfamoylphenyl)benzamide 2,2'-Dithiobis [4'-sulfamoylbenzanilide] (0.1 g, 0.2 mmol) was dissolved in 4 mL of dimethylformamide and 1.6 mL of 2.7% aqueous $NaH_2PO_4$. Dithiothreitol (0.1 g, 0.7 mmol) was added, and the mixture was stirred at 25° C. for 0.5 hours. Formic acid (10 mL 10% aqueous) was added to precipitate the product, which was collected by filtration, washed with water, and with diethyl ether to yield 72 mg of the title compound, mp 230°–231° C.

PREPARATION 30

2-[2-[2-(Carboxymethylcarbamoyl)-phenyldisulfanyl]-benzoylaminol acetic acid

To 18 g (0.24 mol) of glycine in 75 mL of absolute ethanol was added 100 mL of a sodium ethoxide solution prepared from dissolution of 4.6 g (0.2 mol) of sodium. The mixture was cooled to −60° C. and 17.2 g (0.05 mol) of 2,2'-dithiobisbenzoyl chloride was added portionwise. The mixture was brought to room temperature and stirred overnight. The solids were removed by filtration, and the filtrate was acidified with 2N HCl. Solids were collected, dissolved in sodium bicarbonate solution, and the solution filtered. The filtrate was acidified with HCl and the solids collected and dried at 110° C. for 24 hours to give 6.8 g of the title compound, mp 13°–215° C.

PREPARATION 31

2-[2-[2-(1-Carboxy-2-methylpropylcarbamoyl) phenyldisulfanyl]benzoylamino]-3-methylbutanoic acid Using the method employed in Preparation 30, 17.8 g (0.15 mol) of D,L valine was reacted with 17.2 g (0.05 mol) of 2,2'-dithiobisbenzoyl chloride to produce 11.4 g of the title compound after recrystallization from acetic acid, mp 226.5°–227.5° C.

PREPARATION 32

4-[2-[2-(3-Carboxypropylcarbamoyl) phenyldisulfanyl]benzoylaminol butanoic acid

Following the procedure in Preparation 30, 16 g (0.15 mol) of 4-amino-butanoic acid was reacted with 10.8 g (0.03 mol) of 2,2'-dithiobisbenzoyl chloride to afford 7.14 g of the title compound.

PREPARATION 33

8-Chloro-[1,3]dioxolo[4,5-g]quinoline-7-carboxylic acid (2-pyridin-2-yl-ethyl)-amide To 23.3 g (0.10 mol) of 8-hydroxy-[1,3]dioxolo [4,5-g] quinoline-7-carboxylic acid (*J. Med. Chem.*, 1968;11:160) in 500 mL of ethylene chloride was added 35 mL (0.47 mol) of thionyl chloride and 1 mL of DMF. The mixture was heated at reflux overnight, concentrated to 100 mL, and the solids collected to give 18.7 g of 8-chloro-[1,3]dioxolo [4,5-g]quinoline-7-carbonyl chloride, which was used without purification. To 13.5 g (~0.05 mol) of this material in 1000 mL of ethylene chloride was added 10 mL (0.07 mol) of triethylamine and the mixture cooled to 15° C. To this mixture was added 6.25 g (0.51 mol) of 2-(2-aminoethyl) pyridine and the mixture was stirred for 24 hours at room temperature. The reaction was quenched by addition of 500 mL $H_2O$. The organic layer was washed with water, dried ($MgSO_4$), and concentrated to give 16 g of the title compound, mp 145°–146° C.

PREPARATION 34

8-Mercapto-[1,3]dioxolo [4,5g]quinoline-7-carboxylic acid (2-pyridin-2-yl-ethyl)-amide To 10.4 g (0.025 mol) of 8-chloro-[1,3]dioxolo [4,5-glquinoline-7-carboxylic acid (2-pyridin-2yl-ethyl)-amide in 100 mL of ethanol was added 7.2 g (0.1 mol) of sodium hydrogensulfide and the mixture was heated at reflux for 3 hours. The mixture was cooled and the solids filtered, washed with ethanol, and then with water. The filtrate was concentrated and the solids were suspended in water, collected by filtration, and recrystallized from ethanol to give 6.8 g of the title compound, mp 258°–260° C.

PREPARATION 35

4-Chloro-2-phenyl-pyrimidine-5-carboxylic acid (2-diethylamino-ethyl)-amide

Using the procedure of Preparation 33, 15.5 g (0.072 mol) of 4-hydroxy-2-phenyl-pyrimidine-5-carboxylic acid (*J. Med. Chem.*, 1964;7:68) was reacted with 8.5 g (0.073 mol) of 2-diethylaminoethylamine to give 18 g of the title compound after recrystallization from benzene, mp 40°–45° C.

PREPARATION 36

4-Mercapto-2-phenyl-pyrimidine-5-carboxylic acid (2-diethylamino-ethyl)-amide

Using the procedure in Preparation 34, 6.4 g (0.02 mol) of 4-chloro-2-phenyl-pyrimidine-5-carboxylic acid (2-diethylamino-ethyl)-amide was reacted with 4.8 g (0.066 mol) of sodium hydrogen sulfide to afford 4.2 g of the title compound, mp 178°–180° C.

PREPARATION 37

5-Chloro-3-methyl-1-phenyl-1H-pyrazole-4-carboxylic acid (2-pyridine-2-yl-ethyl)-amide Using the procedure in Preparation 33, 28.4 g (0.13 mol) of 5-hydroxy-3-methyl-1-phenyl-1H-pyrazole-4-carboxylic acid was reacted with 15.9 g (0.13 mol) of 2-(2-aminoethyl)

pyridine to produce the title compound, which was used without purification.

PREPARATION 38

5-Mercapto-3-methyl-1-phenyl-1H-pyrazole-4-carboxylic acid (2-pyridin-2-yl-ethyl) amide Using the procedure of Preparation 34, 29.3 g (0.087 mol) of 5-chloro-3-methyl-1-phenyl-1H-pyrazole-4-caboxyclic acid (2-pyridin-2-yl-ethyl)-amide was reacted with 19.3 g (0.27 mol) sodium hydrogen sulfide in cellosolve to give 24.0 g of the title compound, which was used in Example 22 without purification.

PREPARATION 39

4-Chloro-2-dimethylamino-pyrimidine-5-carboxylic acid benzylamide

Using the procedure of Preparation 33, 61.6 g (0.337 mol) of 2-dimethylamino-4-hydroxy-pyrimidine-5-carboxylic acid was reacted with 37 g (0.34 mol) of 2-aminomethyl pyridine to afford 14.3 g of the title compound, which was used without purification.

PREPARATION 40

2-Dimethylamino-4-mercapto-pyrimidine-5-carboxylic acid benzylamide

Using the procedure of Preparation 34, 14.3 g (0.045 mol) of 4-chloro-2-dimethylamino-pyrimidine-5-carboxylic acid benzylamide and 12 g (0.21 mol) of sodium hydrogen sulfide were reacted to give 5.7 g of the title compound, mp 175°–178° C.

PREPARATION 41

4-Chloro-2-phenyl-pyrimidine-5-carboxylic acid benzylamide

Using the procedure of Preparation 33, 31.0 g (0.143 mol) of 4-hydroxy-2-phenyl-pyrimidine-5-carboxylic acid and 60 mL (0.82 mol) of thionyl chloride were reacted to give 37.8 g of crude chloro acid chloride. A 5.0 g (19.8 mmol) portion of the acid chloride was reacted with 2.12 g (19.8 mmol) of benzylamine to give 6.27 g of the title compound, which was used without purification.

PREPARATION 42

4-Mercapto-2-phenyl-pyrimidine-5-carboxylic acid benzylamide

Using the procedure from Preparation 34, 5.8 g (17.9 mol) of 4-chloro-2-phenyl-pyrimidine-5-carboxylic acid benzylamide was reacted with 5.1 g (72 mmol) of sodium hydrogen sulfide to give 3.75 g of the title compound, mp 189°–193° C.

EXAMPLE 1

4-(3-Oxo-3h-benzo [d]isothiazol-2-yl)-benzenesulfonamide

To a solution of 60 mL of methanol and 60 mL of tetrahydrofuran cooled to 0° C. was added dropwise 3.9 g (30.0 mmol) of chlorocarbonylsulfenyl chloride. The mixture was stirred at 0° C. for 20 minutes and then diluted by addition of 9.0 g (29.2 mmol) of 2-thio-N-(4-sulfamoylphenyl)benzamide. The reaction mixture was stirred at 0° C. for 0.5 hours, warmed to room temperature, and stirred for 18 hours. The suspension was diluted with 200 mL of diethyl ether, stirred for 1 hour, and the solid was removed by filtration. After washing with fresh diethyl ether, the solid was dried in vacuo to give 7.8 g of the title compound. An additional 2.2 g was obtained by concentrating the mother liquors and triturating the residue with diethyl ether. The mp of both fractions was 283°–285° C.

EXAMPLE 2

[S (R*,R*)]-3-Methyl-2-(3-oxo-3h-benzo [d] isothiazol-2-yl)pentanoic acid

To a stirred suspension of 5.3 g (10.0 mmol) of [S-(R*, R*)]-2-[2-[2-(1-carboxy-2-methylbutylcarbamoyl) phenyldisulfanylbenzoylamino]-3-methylpentanoic acid (from Preparation 19) in 200 mL of dichloromethane was added dropwise 2.4 g (15.0 mmol) of liquid bromine. The reaction mixture was stirred at room temperature for 2 hours and concentrated to dryness in vacuo. The residue was triturated with dichloromethane. The dichloromethane was removed by evaporation in vacuo to remove excess bromine. The residue was partitioned between dichloromethane/5% aqueous sodium bicarbonate (200 mL each). The aqueous layer was separated, washed with fresh dichloromethane, and acidified to pH 1.5 with 6.0M hydrochloric acid. The acidic aqueous solution was extracted with dichloromethane (2×75 mL). The organic layers were combined, washed with water, dried (MgSO$_4$), filtered and concentrated to dryness in vacuo to give 4.8 g of the title compound, mp 50°–52° C.

EXAMPLE 3

N-Acetyl-4-(3-oxo-3h-benzo [d]isothiazol-2-yl)-benzenesulfonamide/(general method)

A solution of 2,2'-dithiobis-N-[4-[[acetylamino]sulfonyl] phenyl]benzamide (1.0 g, 1.5 mmol) in 1 mL dimethylformamide was diluted with 20 mL dichloromethane, whereupon a fine precipitate formed. Bromine (0.3 g, 1.8 mmol) in 5 mL dichloromethane was added dropwise to the mixture. A homogenous solution gradually formed, and then a solid reformed. The solid was collected by filtration and recrystallized from acetic acid/water (1:1 v/v) to afford 0.6 g of the title compound, mp 254°–255° C.

EXAMPLE 4

N-(3-Oxo-2,3-dihydro-benzo [d]isothiazol-5-yl) -acetamide

Following the general method of Example 3, a slurry of 2,2'-dithiobis [5-acetylamino]benzamide (2.0 g, 4.8 mmol) in 4 mL dimethyl sulfoxide and 20 mL dichloromethane was reacted with bromine (0.8 g, 5.0 mol) in 10 mL of dichloromethane. The solid product was collected by filtration and recrystallized from 5 mL of hot acetic acid to yield 0.8 g of the title compound.

EXAMPLE 5

4-(5-Methoxy-3-oxo-3h-benz[d]isothiazol-2-yl)-benzenesulfonamide

Following the general method of Example 3, a slurry of 2,2'-dithiobis(4-sulfamoyl(5-methoxybenzanilide)) (0.8 g, 1.2 mmol) in 2 mL dimethylformamide and 20 mL dichloromethane was reacted with bromine (0.2 g, 1.3 mmol) in 10 mL dichloromethane. The crude product was recrystallized from methanol/water to afford 0.2 g of the title compound.

EXAMPLE 6

4-(6-Methyl-3-oxo-3h-benzo [d]isothiazol-2-yl)-benzenesulfonamide

Following the general method of Example 3, a slurry of 2,2'-dithiobis [4'-sulfamoyl(4-methylbenz anilide)] (2.1 g, 3.2 mmol) (from Preparation 11) in 4 mL dimethylformamide/40 mL dichloromethane was reacted with bromine (0.6 g, 3.6 mmol) in 15 mL dichloromethane. The crude product was recrystallized from dimethylformamide/water to yield 0.9 g of the title compound.

EXAMPLE 7

4-(6-Fluoro-3-oxo-3h-benzo [d]isothiazol-2-yl)-benzenesulfonamide

Following the general method of Example 3, a slurry of 2,2'-dithiobis [4'-sulfamoyl(4-fluorobenz anilide)] (1.8 g, 2.7 mmol) (from Preparation 12) in 4 mL dimethylformamide and 30 mL dichloromethane was reacted with bromine (0.5 g, 3.2 mmol) in 20 mL of dichloromethane. The crude product was recrystallized from dimethylformamide/water to yield 1.1 g of the title compound, mp 265°–266° C.

EXAMPLE 8

4-(5-Methyl-3-oxo-3h-benzo [d]isothiazol-2-yl)-benzenesulfonamide

Following the general method of Example 3, a slurry of 2,2'-dithiobis [4'-sulfamoyl(5-methylbenzanilde)] (1.1 g, 1.7 mmol) (from Preparation 13) in 2 mL dimethylformamide and 20 mL dichloromethane was treated with bromine (0.3 g, 1.9 mmol) in 10 mL dichloromethane. The crude compound was recrystallized from dimethylformamide/water to afford 0.4 g of the title compound.

EXAMPLE 9

(S)-4-Methyl-2-(6-methoxy-3-oxo-3h-benzo [d] isothiazol-2-yl)-pentanoic acid

Following the general method of Example 3, a slurry of {[s-(R*,R*)]-2-[2-[2-(1-carboxy-3-methyl-butylcarbamoyl)-5-methoxyphenyldisulfanyl]-4-methoxybenzoylamino}]-4-methyl-pentanoic acid (1.4 g, 2.3 mmol) (from Preparation 20) in 4 mL of acetonitrile and 10 mL dichloromethane was treated with bromine (0.4 g, 2.6 mmol) in 10 mL dichloromethane. The crude product was recrystallized from methanol/water to afford 0.8 g of the title compound.

EXAMPLE 10

(S) -4-Methyl-2-(5-fluoro-3-oxo-3h-benzo [d] isothiazol-2-yl) -pentanoic acid

Following the general method of Example 3, a slurry of {8-(R*,R*)]-2-{-[2-(1-carboxy-3-methyl-butylcarbamoyl)-4-fluorophenyldisulfanyl]-5-fluorobenzoylamino}-4-methyl-pentanoic acid (2.1 g, 3.6 mmol) (from Preparation 21) in 8 mL acetonitrile and 25 mL dichloromethane was treated with bromine (0.7 g, 4.4 mmol) in 15 mL dichloromethane. The crude compound was recrystallized from methanol/water to afford 1.4 g of the title compound, mp 161°–162° C.

EXAMPLE 11

(S) -4-Methyl-2-(6-methyl-3-oxo-3h-benzo [d] isothiazol-2-yl)-pentanoic acid

Following the general method of Example 3, a slurry of [s-(R*,R*)]-2-[-[2-(1-carboxy-3-methyl-butylcarbamoyl)-4-methylphenyldisulfanyl)-5-methylbenzoylamino]-4-methyl-pentanoic acid (1.8 g, 3.2 mmol) (from Preparation 22) in 5 mL acetonitrile and 20 mL dichloromethane was reacted with bromine (0.6 g, 3.7 mmol) in,10 mL dichloromethane. The crude product was recrystallized from methanol/water to afford 1.3 g of the title compound.

EXAMPLE 12

(S) -4-Methyl-2-(3-oxo-3h-isothiazolo [5,4-b] pyridin-2-yl) -pentanoic acid

Following the general method of Example 3, a slurry of {[S-(R*,R*)]-2-(2-[3-(1-carboxy-3-methyl-butylcarbamoyl)-pyridin-2-yl-disulfanyl] -pyridine-3-carbonyl}-amino)-4-methyl-pentanoic acid (2.1 g, 4.1 mmol) (from Preparation 23) in 3 mL acetonitrile and 10 mL dichloromethane was reacted with bromine (0.3 g, 1.8 mmol) in 8 mL dichloromethane. The crude compound was recrystallized from methanol/water to yield 0.3 g of the title compound.

EXAMPLE 13

2-(3-Oxo-3h-benzo [d]isothiazol-2-yl)acetic acid

To 6.0 g (13.3 mmol) of 2-[2-[2-carboxylmethyl carbamoyl]phenyldisulfanyl]benzoylamino] acetic acid (from Preparation 30) suspended in 50 mL of $CCl_4$ was added dropwise 0.83 mL (16.1 mmol) of bromine in 15 mL of $CCl_4$ over 1 hour. The solids were removed by filtration. A 6.0 g portion was heated at reflux in 25 mL of acetic acid for 1 hour. The mixture was cooled, and the solids were collected by filtration. Recrystallization from 90! methyl cellosolve, followed by drying at 50° for 24 hours gave 3.0 g of the title compound, mp 236°–238° C.

EXAMPLE 14

3-Methyl-2-(3-oxo-3h-benzo [d]isothiazol-2-yl)-butanoic acid

Following the procedure of Example 13, 6.0 g (13.6 mol) of 2-[2-[2-(1-carboxy-3-methylbutyl carbamoyl) phenyldisulfanyl]benzoylamino)-3-methylbutanoic acid was reacted with bromine to provide 2.25 g of the title compound, mp 166°–168° C.

EXAMPLE 15

2-Phenyl-3-oxo-3h-benz[d]isothiazole

Using the procedure from Example 13, 20 g (43.7 mmol) of 2,2'-dithiobisbenzanilide (prepared as described in *J Med.*

*Chem.*, 1985;28:1772) was reacted with bromine to give 10.55 g of crude isothiazole. Crystallization from absolute ethanol, and then isopropanol gave 5.4 g of 3-phenyl-3-oxo-3h-benz [d]isothiazole, mp 143°–145° C.

EXAMPLE 16

2-(4-Acetylphenyl)-3-oxo-3h-benz [d]isothiazole

To 7.0 g (12.9 mmol) of 2,2'-dithiobis [4'48 -acetyl (benzanilide)] in 50 mL of $CCl_4$ was added dropwise over 1 hour a solution of 0.7 mL (13.5 mmol) of bromine in 5 mL of $CCl_4$. The solid precipitate was collected by filtration. A 1.3 g portion of the solid was slurried in sodium bicarbonate solution for 30 minutes. The solid was collected by filtration and dried at 70° C. for 24 hours to give 0.87 g of the title compound, mp 183°–185° C.

EXAMPLE 17

4-(3-Oxo-2-h-benzo [d]isothiaz-2-yl) butanoic acid

Using the procedure from Example 13, 2.4 g (5.0 mmol) of 4-[2-[2-(3-carboxypropylcarbamoyl) phenyldisulfanyl] benzoylamino] butanoic acid (from Preparation 32) was reacted with bromine to give 0.85 g of the crude isothiazolone, which was recrystallized from isopropanol to give 0.76 g of the title compound, mp 97°–99° C.

EXAMPLE 18

2-(4-Methylpyridin-2-yl)-3-oxo-3h-benzo [d] isothiazole

Using the method of Fischer and Hurni (*Arzneimittel Forsch.*, 1964;14:1301) 5.4 g (0.05 mol) of 2-amino-4-methylpyridine in 50 mL of pyridine at 10° C. was reacted with 10.3 g (0.05 mol) of 2-chlorosulfenylbenzoyl chloride. The mixture was heated to 50° C. and maintained at that temperature for 2 hours. The mixture was cooled to 25° C. and filtered. The solid was recrystallized from benzene to give 4.5 g of the title compound, mp 195°–196.5° C.

EXAMPLE 19

4-(3-Oxo-3h-benzo [d]isothiazol-2-yl) phenylacetic acid

To a mixture of 7.55 g (0.05 mol) of 4-aminophenylacetic acid and 15.15 g (0.15 mol) of triethylamine in 25 mL of ethyl cellosolve was added 10.3 g (0.05 mol) of 2-chlorosulfenylbenzoyl chloride (*Arzneimittel Forsch.*, 1964;14:1301). The mixture was stirred at room temperature for 3 hours, concentrated in vacuo, and water was added to the residue. The mixture was acidified with HCl and filtered to give 9.9 g of the title compound, mp 173°–175° C.

EXAMPLE 20

2-[2-(2-Pyridinyl)ethyl]-[1,3]dioxolo [4,5-a] isothiazolo [4,5-c]quinolin-3(2H)-one To 4.1 g (0.012 mol) of 8-mercapto-[1,3]dioxolo [4,5-g] quinoline-7-carboxylic acid (2-pyridin-2-yl-ethyl)-amide (from Preparation 34) and 5 mL (0.035 mol) of triethylamine in 750 mL of methanol was added 2.95 g (0.012 mol) of iodine in 100 mL of methanol. The mixture was heated at reflux for 2 hours, cooled, and then concentrated to an oil. The residue was slurried in water, and the solid was collected and recrystallized in ethanol to give 3.5 g of the title compound, mp 200°–201° C.

EXAMPLE 21

2-[2-(Diethylamino)ethyl]-6-phenyl-isothiazolo[5,4-d]pyrimidin-3(2H)-one

Using the procedure of Example 20, 3.3 g (0.01 mol) of 4-mercapto-2-phenyl-pyrimidine-5-carboxylic acid (2-diethylamino-ethyl)-amide (from Preparation 36) and 2.54 g (0.01 mol) of iodine were reacted to give 2.25 g of the title compound after recrystallization from isopropanol, mp 106°–107° C.

EXAMPLE 22

3-Methyl-1-phenyl-5-[2-(2-pyridinyl)ethyl]-1H-pyrazolo [4,5-d]isothiazol-4(5H)-one Using the procedure of Example 20, 24 g (0.069 mol) of 5-mercapto-3-methyl-1-phenyl-1H-pyrazole-4-carboxylic acid (2-pyridin-2-yl-ethyl)amide (from Preparation 38) was reacted with 17.6 g (0.069 mol) of iodine to give 4.8 g of the title compound after two recrystallizations from isopropanol, mp 137°–138° C.

EXAMPLE 23

6-(Dimethylamino)-2-(2-pyridinylmethyl)isothiazolo [5,4-d]pyrimidin-3-(2H)-one

Using the procedure of Example 20, 5.7 g (0.02 mol) of 2-dimethylamino-4-mercapto pyrimidine-5-carboxylic acid benzylamide (from Preparation 40) was reacted with 5.0 g (0.02 mol) of iodine to give 2,27 g of the title compound after crystallization from ethanol, mp 145°–146° C.

EXAMPLE 24

2-Benzyl-6-phenyl-isothiazolo [5,4-d]pyrimidin-3-one

Using the procedure of Example 20, 2.0 g (6.22 mmol) of 4-mercapto-2-phenyl-pyrimidine-5-carboxylic acid benzylamide (from Preparation 42) was reacted with 1.74 g (6.8 mmol) of iodine to give 1.74 g of the title compound after crystallization from isopropanol, mp 166°–167° C.

EXAMPLE 25

4-(3-Oxo-3h-benz-[d]isothiazol-2-yl) -phenyl acetic acid

Using the procedure of Example 13, 1.5 g (2.6 mol) of 4-[2-[2-(4-carboxymethylphenylcarbamoyl) phenyldisulfanyl]benzoylamino] phenylacetic acid was reacted with bromine to give 0.62 g of the title compound, mp 173°–175° C.

EXAMPLE 26

(S)-2,6-Bis-(3-oxo-3H-benzo [d]isothiazol-2-yl)-hexanoic acid methyl ester

Using the procedure from Example 18, 0.77 g (3.3 mmol) of lysine methyl ester dihydrochloride and 2.1 mL (15 mol)

of triethylamine in 60 mL of dichloromethane was reacted with 1 g (3.0 mmol) of 2-chlorosulfenylbenzoyl chloride. The mixture was stirred at room temperature for 18 hours, then the solution was washed with 1N HCl, saturated NaHCO$_3$, and brine. The solution was dried and concentrated to give 1 g of an oil. The compound was purified by chromatography (SiO$_2$, CHCl$_3$-CHCl$_3$/MEOH; 98/2) to give 0.16 g of the title compound as a glass.

NMR (DMSO): δ8.03 (m, 2H), 7.61 (m, 2H), 7.50 (m, 2H), 7.41 (m, 2H), 5.42 (m, 1H), 3.88 (t, 2H), 3.75 (s, 3H), 2.24 (m, 1H, 2.11 (m, 1H, 1.87 (m, 2H), 1.44 (m, 2H).

EXAMPLE 27

2-(2-Morpholin-4-yl-ethyl)-6-phenyl-isothiazolo[5,4-d) pyrimidin-3-one

Using the procedure of Example 20, 2.0 g (5.81 mmol) of 4-mercapto-2-phenyl-pyrimidine-5-carboxylic acid (2-morpholin-4-yl-ethyl)-amide were treated with 1.47 g (5.81 mmol) of iodine to give 1.21 g of the title compound after recrystallization from isopropanol, mp 163°–165° C.

EXAMPLE 28

2-Phenethyl-6-phenyl-isothiazolo [5,4-d]pyrimidin-3-one

Using the procedure of Example 20, 2.0 g (5.96 mmol) of 4-mercapto-2-phenyl-pyrimidine-5-carboxylic acid phenethyl-amide were treated with 1.66 g (6.56 mmol) of iodine to give 1.42 g of the title compound after recrystallization from isopropanol, mp 144°–147° C.

EXAMPLE 29

6-Phenyl-2-pyridin-2-ylmethyl-isothiazolo[5,4-d] pyrimidin-3-one

Using the procedure of Example 20, 2.0 g (6.20 mmol) of 4-mercapto-2-phenyl-pyrimidine-5-carboxylic acid (pyridin-2-ylmethyl)-amide were treated with 1.73 g (6.82 mmol) of iodine to give 1.62 g of the title compound after recrystallization from isopropanol, mp 154°–156° C.

EXAMPLE 30

6-Phenyl-2-(2-pyridin-2-yl-ethyl) -isothiazolo[5,4-d] pyrimidin-3-one

Using the procedure of Example 20, 14.0 g (41.6 mmol) of 4-mercapto-2-phenyl-pyrimidine-5-carboxylic acid (2-pyridin-2-yl-ethyl)-amide were treated with 10.6 g (41.7 mmol) of iodine to give 12.7 g of the title compound after recrystallization from ethanol, mp 132°–133° C.

EXAMPLE 31

6-Piperidin-1-yl-2-(2-pyridin-2-yl-ethyl) -isothiazolo [5,4-d] pyrimidin-3-one

Using the procedure of Example 20, 33.0 g (96.2 mmol) of 4-mercapto-2-piperidin-1-yl-pyrimidine-5-carboxylic acid (2-pyridin-2-yl-ethyl)-amide were treated with 24.4 g (96.1 mmol) of iodine to give 21.4 g of the title compound after recrystallization from aqueous ethanol, mp 109°–110° C.

EXAMPLE 32

6-Piperidin-1-yl-isothiazolo [5,4-d]pyrimidin-3-one

Using the procedure of Example 20, 20.8 g (87.4 mmol) of 4-mercapto-2-piperidin-1-yl-pyrimidine-5-carboxylic acid amide were treated with 22,2 g (87.4 mmol) of iodine to give 14.37 g of the title compound after recrystallization from dimethyl-formamide, mp 268°–269° C.

EXAMPLE 33

6-Morpholin-4-yl-2-(2-piperidin-1-yl-ethyl)-isothiazolo [5,4-d]pyrimidin-3-one

Using the procedure of Example 20, 5.2 g (14.8 mmol) of 4-mercapto-2-morpholin-4-yl-pyrimidine-5-carboxylic acid (2-piperidin-1-yl-ethyl)-amide were treated with 3.81 g (15.0 mmol) of iodine to give 2.6 g of the title compound after recrystallization from aqueous isopropanol, mp 98°–100° C.

EXAMPLE 34

6-Dimethylamino-2-(2-pyridin-2-yl-ethyl)-isothiazolo [5,4-d]pyrimidin-3-one

Using the procedure of Example 20, 7.5 g (24.8 mmol) of 2-dimethylamino-4-mercapto-pyrimidine-5-carboxylic acid (2-pyridin-2-yl-ethyl)-amide were treated with 6.4 g (25.2 mmol) of iodine to give 4.21 g of the title compound after recrystallization from isopropanol, mp 134°–136° C.

EXAMPLE 35

6-Dimethylamino-2-(2-piperidin-1-yl-ethyl)-isothiazolo [5,4-d]pyrimidin-3-one

Using the procedure of Example 20, 6.2 g (20.1 mmol) of 2-dimethylamino-4-mercapto-pyrimidine-5-carboxylic acid (2-piperidin-1-yl-ethyl)-amide were treated with 5.08 g (20.0 mmol) of iodine to give 5.31 g of the title compound after recrystallization from ethyl acetate, mp 128°–129° C.

Additional isothiazolones which can be made utilizing the processes described above include the following:

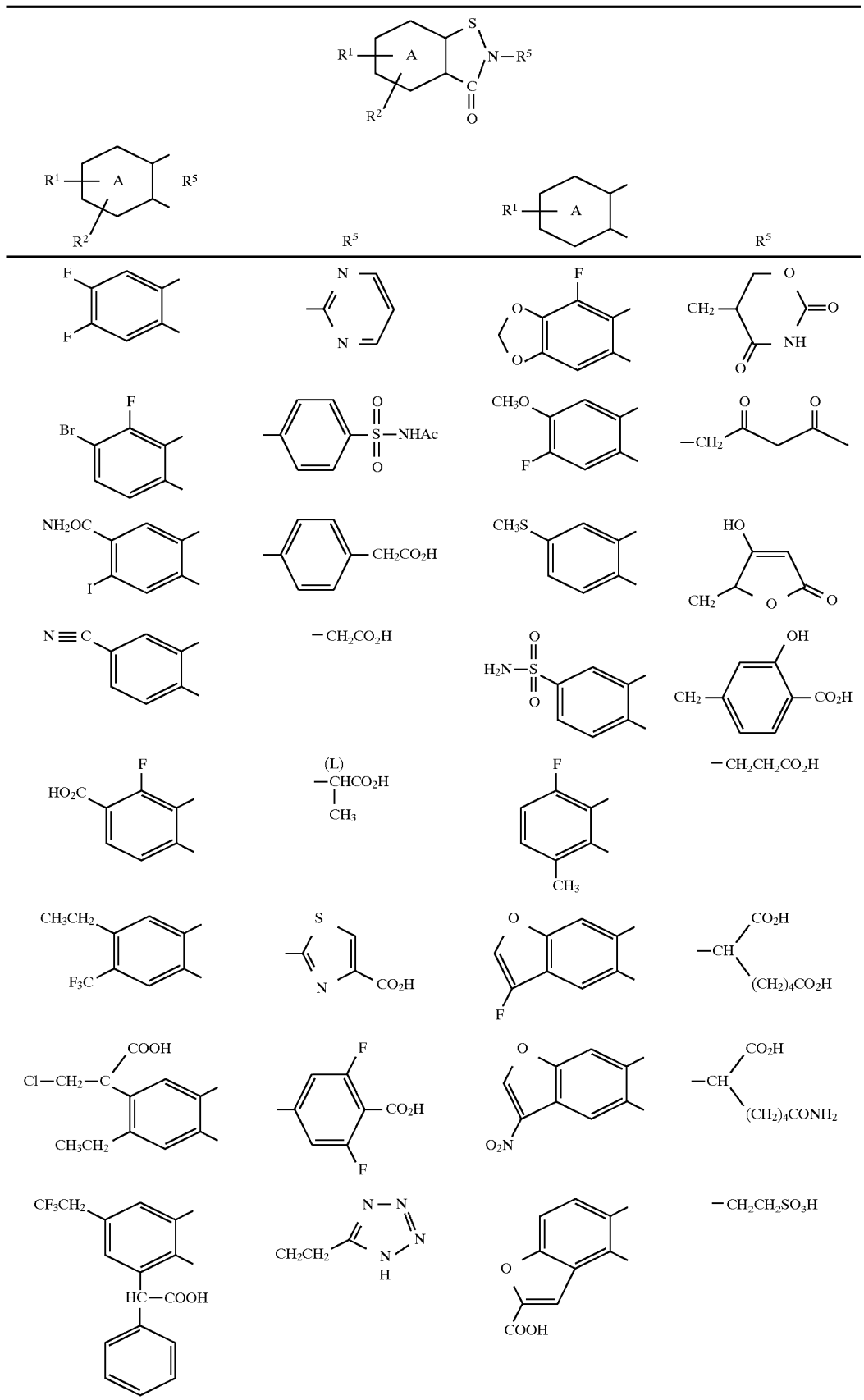

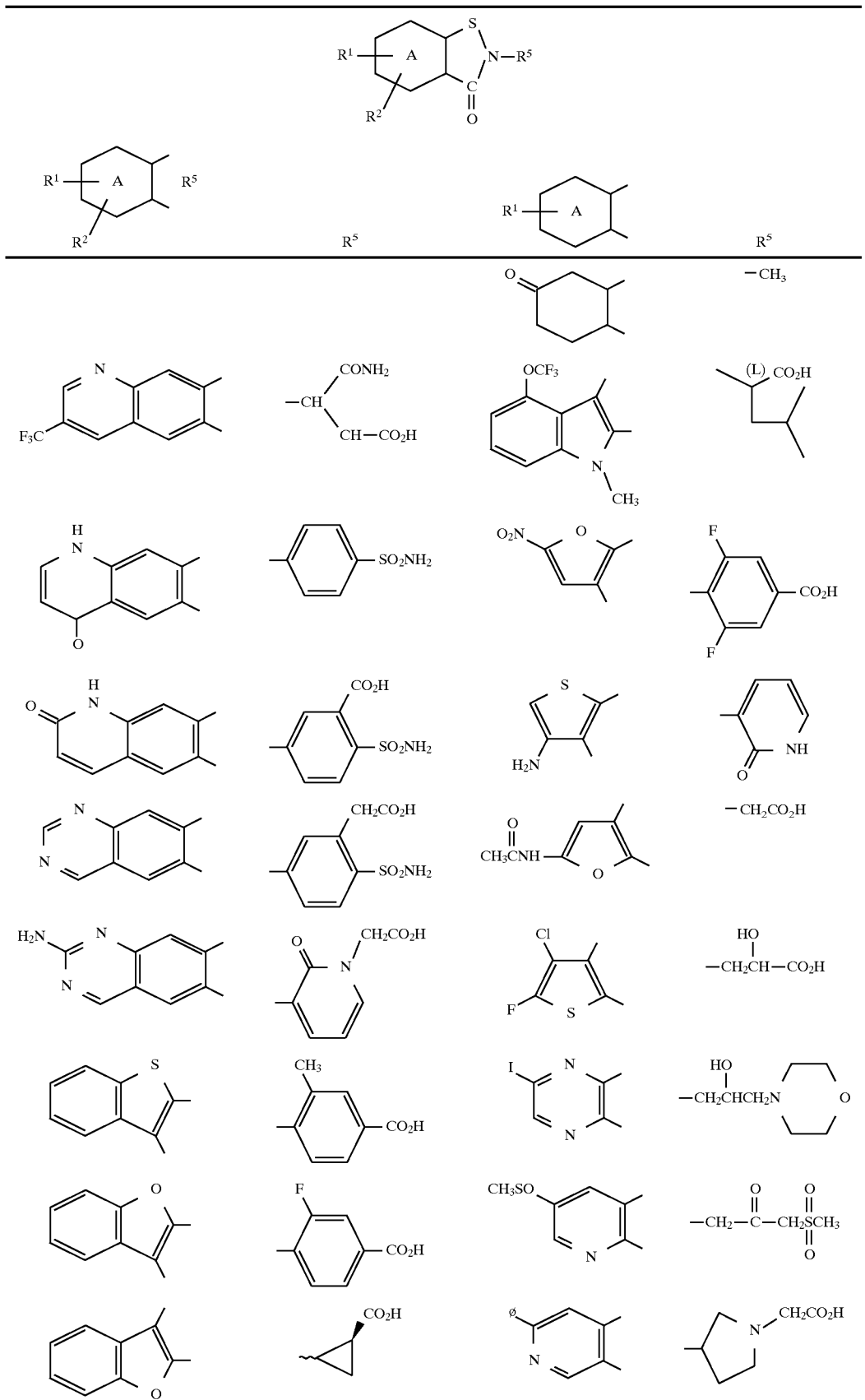

-continued
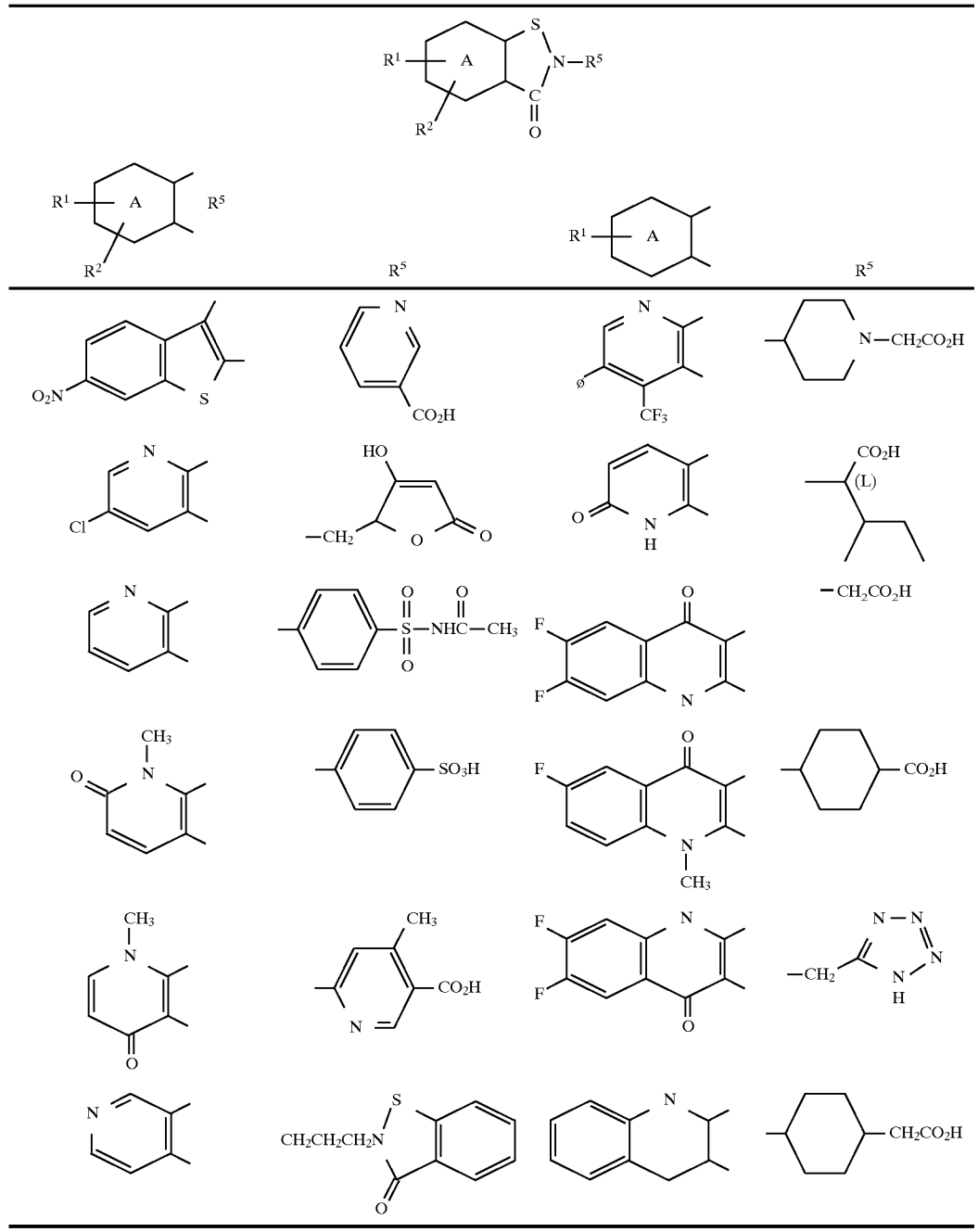
Additional specific isothiazolones according to this invention include the following:

| Example | R¹ | R² | R⁵ |
|---|---|---|---|
| 36 | H | H | —CHiPrCOOH |
| 37 | H | H | n-hexyl |
| 38 | H | H | —CH₂COOEt |
| 39 | H | H | -phenyl |
| 40 | H | H | 4-acetylphenyl |
| 41 | H | H | acetyl |
| 42 | H | H | benzoyl |
| 43 | H | H | C(S)NH phenyl |
| 44 | H | H | 4-chlorobenzoyl |
| 45 | H | H | 4-nitrobenzoyl |
| 46 | H | H | CO(CH₂)₄CH₃ |
| 47 | H | H | COCH₂phenyl |
| 48 | H | H | COCH₂—N(phthalimido) |
| 49 | H | H | 4-methoxybenzoyl |
| 50 | H | H | 1-hydroxycarbonyl-2-methylbutyl |
| 51 | H | H | 2-ethoxycarbonyl benzoyl |
| 52 | H | H | 2-chlorobenzoyl |
| 53 | H | H | 4-methyl-2-pyridyl |
| 54 | H | H | 5-nitrothiazolon-2-yl |
| 55 | H | H | 2-(4-nitrophenyl)-2-hydroxy-1-hydroxy methylethyl |
| 56 | H | H | 3-hydroxycarbonyl propyl |
| 57 | H | H | 2-hydroxycarbonyl benzyl |
| 58 | H | H | 2-pyrrolidin-1-ylethyl |
| 59 | 5-CH₃O | 6-CH₃O | 2-(2-pyridyl)ethyl |
| 60 | H | H | 2-(2-piperidyl)ethyl |
| 61 | H | H | 3-(1-piperidyl)propyl |
| 62 | H | H | 4-hydroxycarbonyl methylphenylbenzyl |
| 63 | H | H | 4-methoxybenzyl |
| 64 | H | H | 4-methoxyphenyl |
| 65 | H | H | 2,4-dichlorophenyl |
| 66 | H | H | 2,4-dichlorobenzyl |
| 67 | H | H | 3,4-dichlorophenyl |
| 68 | H | H | 3,4-dichlorobenzyl |
| 69 | H | H | 4-chlorophenyl |
| 70 | H | H | 4-chlorobenzyl |
| 71 | H | H | 4-(N-acetylamino) phenyl |
| 72 | H | H | 4-(N-acetylamino) benzyl |
| 73 | H | H | 4-ethoxycarbonylphenyl |
| 74 | H | H | 4-ethoxycarbonylbenzyl |
| 75 | H | H | 4-tert-butylphenyl |
| 76 | H | H | 4-tert-butylbenzyl |
| 77 | H | H | 4-trifluoromethyl phenyl |
| 78 | H | H | 4-trifluoromethyl benzyl |
| 79 | H | H | 4-biphenyl |
| 80 | H | H | 4-phenylbenzyl |
| 81 | H | H | 4-nitrobenzyl |
| 82 | H | H | cyclopropyl |
| 83 | H | H | cyclopropylmethyl |
| 84 | H | H | 2-phenylethyl |
| 85 | H | H | cyclohexyl |
| 86 | H | H | cyclohexylmethyl |
| 87 | H | H | 4-aminosulfonylphenyl |

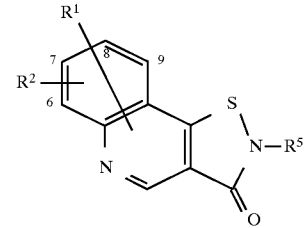

| Example | R¹ | R² | R⁵ | mp °C. |
|---|---|---|---|---|
| 88 | H | H | n-propyl | |
| 89 | H | H | 2-(2-pyridyl)ethyl | |
| 90 | H | H | 2-(N,N-diethylamino)ethyl | |
| 91 | 7-chloro | 8-chloro | dimethylaminoethyl | 241–242 |
| 92 | 6-methoxy | 9-chloro | 2-dimethylaminoethyl | 172–173 |
| 93 | H | 7-methoxy | 2-dimethylaminoethyl | 175–176 |
| 94 | H | 8-methoxy | 2-dimethylaminoethyl | 155–156 |
| 95 | | 7,8-methylene dioxy | 3-dimethylaminopropyl | 160–161 |
| 96 | | 7,8-methylene dioxy | 2-pyrrolidinoethyl | 185–186 |
| 97 | | 7,8-methylene dioxy | 2-morpholinoethyl | 200–202 |
| 98 | H | 8-chloro | 2-dimethylaminoethyl | 214–215 |
| 99 | | 7,8-methylene dioxy | 2-acetamidoethyl | >260 |
| 100 | 7-chloro | 8-methoxy | 2-dimethylaminoethyl | 226–227 |

| Example | R¹ | R² | R⁵ |
|---|---|---|---|
| 101 | H | 6-piperidino | 2-(N,N-diethylamino)ethyl |
| 102 | H | 6-piperidino | 2-(2-pyridyl)ethylhydro chloride |
| 103 | H | 6-dimethylamino | 2-piperidylmethyl |
| 104 | H | 6-pyrrolidino | 2-(2-pyridyl)ethyl |
| 105 | H | 6-phenylsulfonyl | 2-dimethylamino ethyl |
| 106 | H | 6-chloro | methyl |
| 107 | H | 6-trifluoromethyl | cyclopropyl |
| 108 | H | 6(3,4-dimethoxyphenyl) | 2-dimethylamino ethyl |

-continued

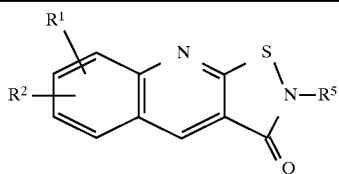

| Example | R¹ | R² | R⁵ | mp °C. |
|---|---|---|---|---|
| 109 | H | H | 2-dimethylaminoethyl | 86–87 |

The compounds of the present invention cause the extrusion of zinc from the nucleocapsid protein (NCp7) of HIV-1. The NC protein is highly conserved among all retroviruses (South T., Blake P., et al., *Biochemistry,* 1990;;29:7786) and is essential for viral infectivity (Aldovini A. and Young R., *J. Virology,* 1990;64:1920 and Gorelick R., Nigida S., et al., *J. Virology,* 1990;64:3207). The zinc is normally held in NC proteins by 1 or 2 zinc fingers. In the case of HIV-1, 2 zinc fingers are present (Summers M., South T., et al., *Biochemistry,* 1990;29:329) and are involved specifically with the PSI site on viral RNA which controls the packaging of viral RNA. Interference of this packaging causes the formation of non-infectious virions (Dannull J., Surovoy A., et al., *EMBO,* 1994;13:1525). It has previously been shown that compounds that cause zinc extrusion have potent anti-HIV activity in multiple cell lines and against all retroviruses (Rice W., Schaeffer C., et al., *Nature,* 1993;361:473).

A fluorescence-based assay has been developed to monitor the ejection of zinc from purified HIV-1 NCp7. The fluorophore, N-(6-methoxy-8-quinolyl)-p-toluenesulfonamide (TSQ), has an increased fluorescent signal upon bonding zinc ion in solution. The NCp7 protein containing 2 Zn-fingers and 2 Zn ions is incubated with drug causing the extrusion of Zn ions. The released Zn is then sequestered by the TSQ and the increased fluorescence monitored relative to control. The assay was performed as follows: 10 $\mu$M compound was added to 2.8 $\mu$M NCp7 and 47 $\mu$M TSQ in 20 $\mu$L of pH 7.4 buffer at 26° C. for 90 minutes. Fluorescence (excitation 355 nM emission 400 nM) was monitored versus time. Controls were the NCp7 under assay conditions without drug, and apo NCp7 (no Zn) with drug. The % Zn extrusion was calculated based on the actual fluorescence measured divided by the fluorescence of all theoretical Zn extruded (5.6 $\mu$M)×100.

Electrospray ionization mass spectral analysis was also performed. Using 40 $\mu$M NCp7 in ammonium acetate buffer at pH 6, 320 $\mu$M 4-(3-oxo-3h-benzo[d]isothiazol-2-yl) benzenesulfonamide (Example 1) in acetonitrile was added. After 3 minutes, a mass peak at 6360 (100%) corresponding to apo NCp7 (loss of 2 Zn) appeared. In addition, a peak at 6740 corresponding to the NCp7+ 308 + Zn appeared. This peak represents the NCp7 with one zinc extruded and a covalently attached compound of 308 MW corresponding exactly to the MW of Example 1 indicating the extrusion of zinc and the formation of a covalent bond between the cysteine of the zinc finger and the isothiazolone.

The test systems utilized to establish the cellular antiviral activity of the isothiazolones of Formula I are well recognized in the art and are routinely employed for such purpose. For example, the assay utilized to evaluate the compounds activity against the HIV virus is that employed by the U.S. National Cancer Institute as described by Weislow O. S., et al., *J. Natl. Cancer Inst.,* .1989;81:577–586, incorporated herein by reference.

The procedure is designed to detect agents acting at any stage of the virus reproductive cycle. The assay basically involves the killing of T4 lymphocytes by HIV. Small amounts of HIV are added to cells, and at least two complete cycles of virus reproduction are necessary to obtain the required cell killing. Agents which interact with virions, cells, or virus gene-products to interfere with viral activities will protect cells from cytolysis. The system is automated in several features to accommodate large numbers of candidate agents, and is generally designed to detect anti-HIV activity. However, compounds which degenerate or are rapidly metabolized in the culture conditions may not show activity in this screen.

Another test system utilized to evaluate the invention compounds is called HIV H9 assay. The HIV H9 cell assay measures the inhibitor concentration required to suppress HIV-1 virus replication. In this system, viral growth occurs through multiple rounds of the life-cycle. Any suppression of the replication kinetics results in a geometric decrease in virus production. As a result, this assay is a sensitive means of measuring the ability of a compound to inhibit HIV-1 viral replication.

The H9 T-cell line is batch infected with HIV virus at an MOI of 0.01. After 2 hours absorption, the cells are washed, resuspended in RPMI-1640/10% fetal calf serum, and seeded at 5×10−3 cells/well of a 96-well plate. A duplicate plate of uninfected H9 cells is prepared for the cytotoxicity assay. Drugs are serially diluted 1/3.16 in DMSO, transferred to media at an 8× concentration, and then added to the cultures in triplicate. The final DMSO concentration of 0.002 (0.2%).

Viral production is measured by RT assay and cytotoxicity is measured by XTT assay at 7 days post-infection. The RT assay is performed as a modification of Borroto-Esoda and Boone, *J. Virol.,* 1991;65:1952–1959 and quantitated using a Molecular Dynamics Phosphoimager with Imagequant software. The XTT assay is performed as a modification of Roehm, et al., *J. Immuno. Methods.,* 1991;142:257–265 and quantitated using a molecular Devices Thermomax plate reader with Softmax software.

Data is electronically transferred to a Microsoft Excell spreadsheet for analysis. The RT assay values equivalent to 50% and 90% inhibition of virus production are calculated from the untreated controls. The concentrations of inhibitor required to produce these values ($IC_{50}$ and $IC_{90}$) are interpolated from data points flanking these RT activities. The XTT assay values equivalent to 50% cytotoxicity are calculated from the untreated controls. The concentrations of inhibitor required to produce this value are interpolated from data points flanking these XTT values.

Yet another test system employed to determine antiviral activity is called the CEM cell assay.

T4 lymphocytes (CEM cell line) are exposed to HIV at a virus to cell ratio approximately 0.05, and plated along with noninfected control cells in 96-well microliter plates.

Candidate agent is dissolved in dimethyl sulfoxide (unless otherwise noted), then diluted 1:200 in cell culture medium. Further dilutions (half-$log_{10}$) are prepared before adding to an equal volume of medium containing either infected or noninfected cells.

Cultures are incubated at 37° in a 5% carbon dioxide atmosphere for 6 or 7 days. The tetrazolium salt, XTT, is added to all wells, and cultures are incubated to allow formazan color development by viable cells *J. National Cancer Institute,* 1989;81:577–586. Individual wells are analyzed spectrophotometrically to quantitate formazan production, and in addition are viewed microscopically for detection of viable cells confirmation of protective activity.

Drug-tested virus-infected cells are compared with drug-treated noninfected cells and with other appropriate controls (untreated infected and untreated noninfected cells, drug-contain wells without cells, etc.) on the same plate. Data are reviewed in comparison with other tests done at the same time and a determination about activity is made.

Table 1 below presents the results of testing several of the invention compounds in zinc extrusion assay described above. The compounds were evaluated for their ability to cause the extrusion of zinc from nucleocapsid protein NCp7 (expressed as % relative to control).

TABLE 1

Zn Extrusion From the Zn Fingers of
HIV-1 Nucleocapsid Protein (NCp7)

| Compound of Example | % Zn Extrusion Relative to Control |
|---|---|
| EDTA[a] | 10 |
| Preparation 29 | 5.8 |
| 1 | 100 |
| 2 | 30 |
| 13 | 75 |
| 14 | 71 |
| 15 | 97 |
| 17 | 78 |
| 18 | 100 |
| 25 | 89 |

[a]EDTA removes approximately 10% of the Zn from the Zn finger in 24 hours (Rice W. and Schaeffer C., et al., Nature, 1993;361:473)

Table 2 below presents data for several invention compounds when evaluated in the H9 and the CEM cell assays. The data establish the compounds of this invention are effective against the HIV virus when evaluated in both test systems.

TABLE 2

Anti-HIV Activity

| Compound of Example | CEM Cell Assay | |
|---|---|---|
| | $EC_{50}$ (uM)[a] | $TC_{50}$ (uM)[b] |
| 1 | 5.1 | 21 |
| 2 | 14 | >100 |
| 14 | 21 | >100 |
| 17 | 5.8 | >100 |
| 25 | 5.8 | 69 |

[a]Effective concentration which protects cells from viral cytopathic effects
[b]Toxic concentration which inhibits the growth of cells 50% relative to control The compounds of the invention have utility against a wide range of retroviral infections, and accordingly, have broad application. Examples of possible viruses that may be suitable for treatment using the present invention include Type C and Type D retroviruses, HTLV-1, HTLV-2, FLV, SIV, MLV, BLV, BIV, equine infectious viruses, anemia viruses, avian sarcoma viruses, and the like.

The isothiazolones of Formula I are also effective for treating inflammation and atherosclerosis. A characteristic feature of atherosclerosis is the accumulation of cholesteryl ester engorged from foam cells. Foam cells are derived from circulating monocytes which invade artery walls in response to hypercholesterolemia, and mature into tissue macrophages. The enzyme 15-lipoxygenase (15-LO) has been implicated in inflammatory disorders and in the origin and recruitment of foam cells (see Harats, et al., *Trends Cardioivasc. Med.*, 1995;5(1):29–36. This enzyme is capable of oxidizing esterified polylnoic fatty acids, such as those found in phospholipids. Treatment of experimental animals with antioxidants which reduce hydroperoxides produced by 15-LO has been shown to retard the progression of atherosclerotic lesions. Accordingly, administering compounds which inhibit 15-LO is an effective way to treat and prevent atherosclerosis. The isothiazolones of Formula I are effective inhibitors of 15-LO when evaluated in standard assays routinely utilized to measure 15-LO activity. Specifically, representative compounds were evaluated by the methods described by Auerbach, et al., *Analytical Biochemistry*, 1992;201:375–380. Two in vitro assays were utilized, both utilizing rabbit reticulocyte 15-LO, and linoleic acid as substrate, to enzymatically produce a peroxide oxidation product known as 13(S)-HPODE. N-Benzoyl leucomethylene blue was utilized as a colorimetric reagent for detection and quantification of the peroxide formation. Also, HPLC was utilized to quantify the oxidation following incubation at 4° C. for 10 minutes.

The 15-LO inhibitory activity of representative isothiazolones is presented in Tables 3 and 4. Table 3 gives the concentration of compound required to inhibit 50% of the activity of 15-LO ($IC_{50}$) when measured by the HPLC method of Auerbach, et al. Table 4 gives the percent inhibition of 15-LO activity when evaluated by the calorimetric method.

TABLE 3

HPLC Assay of 15-LO Inhibition

| Compound of Example | $IC_{50}$ ($\mu$M) |
|---|---|
| 23 | 0.4 |
| 24 | 0.3 |
| 27 | 0.27 |
| 28 | 0.76 |
| 29 | 0.39 |
| 30 | 0.29 |
| 31 | 1.3 |
| 32 | 3.2 |
| 33 | 0.12 |
| 34 | 1.7 |
| 35 | 0.16 |

TABLE 4

Colorimetric Assay of 15-LO Inhibition

| Compound of Example | % Inhibition |
|---|---|
| 1 | 35 @ 10 $\mu$M |
| 3 | 75 @ 10 $\mu$M |
| 21 | 95 @ 10 $\mu$M |
| 50 | >10 $\mu$M |
| 59 | >10 $\mu$M |
| 91 | >10 $\mu$M |
| 93 | >10 $\mu$M |
| 94 | >10 $\mu$M |
| 95 | >10 $\mu$M |
| 96 | >10 $\mu$M |
| 97 | >10 $\mu$M |
| 108 | 65 @ 10 $\mu$M |
| 109 | 22 @ 10 $\mu$M |

The compounds of Formula I are therefore useful for treating atherosclerosis by virtue of their ability to inhibit 15-LO.

In a further embodiment of this invention, the compounds can be formulated into compositions suitable for applying to surfaces such as wood, metal, ceramic, and the like, and for administering to animals, including humans, for treating and preventing diseases caused by viruses, as well as inflammation and atherosclerosis. The compounds can be formulated for administration by any route, for instance orally, parenterally, topically, and rectally. For oral administration, for example, an invention compound can be mixed with an inert diluent or with an assimilable edible carrier, or it may be enclosed in a hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5% to about 80% of the weight of the unit. The amount of active compound in such therapeutically useful compositions is such that a therapeutically effective dosage will be obtained. Preferred compositions or preparations according to the present invention are prepared so that an oral dosage unit form contains between about 5 and 1000 mg of active compound, and ideally about 25 to about 750 mg.

The tablets, troches, pills, capsules, and the like may also contain common pharmaceutical excipients such as binders, sweeteners, and the like. Typical binders include gum tragacanth, acacia, corn starch, and gelatin, as well as excipients such as dicalcium phosphate. Typical disintegrating agents include corn starch, potato starch, alginic acid, and the like. A commonly used lubricant is magnesium stearate. Typical sweetening agents are sucrose, lactose, or saccharin, and flavoring agents such as peppermint, oil of wintergreen, or cherry flavoring can be utilized. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup or elixir may contain the active compound, sucrose as a sweetening agent, methyl and propylparabens as preservatives, a dye, and flavoring such as cherry or orange flavor. Of course, any material used in preparing any dosage unit form should be pharmaceutically pure and substantially nontoxic in the amounts employed.

The isothiazolone compounds of the invention can also be formulated for topical administration, for instance as patches, salves, creams, ointments, and the like. Agents commonly utilized to enhance transdermal passage can also be employed. The compounds can also be formulated with waxes and the like for convenient rectal administration.

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a polyol (for example, glycerol, propylene glycol, and liquid polyethylene glycol, and the like), suitable mixtures thereof, and vegetable oils. The proper fluidity can be maintained, for example, by the use of a coating such as lecithin; by the maintenance of the required particle size in the case of dispersion and by the use of surfactants the prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. The term "effective amount" means that quantity of isothiazolone which has a positive therapeutic effect for treating the viral infection, the inflammation, or the atherosclerosis which affects the mammal to be treated. A unit dosage form can, for example, contain the principal active compound in amounts ranging from about 5 to about 1000 mg, with from about 25 to about 750 mg being preferred. A typical dose will be about 50 to about 500 mg. In the case of compositions containing supplementary active ingredients, the dosages are determined by reference to the usual dose and manner of administration of the said ingredients. The unit dosages typically will be administered from one to four times per day, or as otherwise needed to effect treatment of the disease state.

In a further embodiment, the isothiazolones are utilized in combination with other agents having antiviral activity. For example, commonly used agents include acyclovir, AZT (azidothymidine, zidovudine), ribavirin, vidarabine, ganciclovir dideoxyinosine (ddI), and the like. The isothiazolones will be administered in combination with such other antiviral agents generally in their respective normal dosing regimens. The specific combinations to be utilized, the respective amounts administered, and the frequency of dosing will, of course, be determined by the attending medical technician or physician in view of the particular agents employed, the specific condition being treated, and the severity of the disease.

The following examples further illustrate the formulations of this invention.

EXAMPLE 110

Soft gelatin capsules were prepared using the following ingredients:

|  | Qunatity (mg/capsule) |
| --- | --- |
| Compound of Example 1 | 250.0 |
| Butylated hydroxyanisole B.P. | 0.05 |
| Fractioned Coconut Oil B.P. | 70.0 |
|  | 320.05 |

The above ingredients were mixed and filled into a soft gelatin capsule, the shell components of which were gelatin and glycerine. The capsules are administered at the rate of one to four times a day.

EXAMPLE 111

Tablets are prepared using the following components:

| Compound of Example 5 | 500 mg |
| --- | --- |
| Microcrystalline Cellulose | 200 mg |
| Sodium Carboxymethyl Starch | 20 mg |
| Magnesium Stearate | 4 mg |
| Butylated Hydroxyanisole B.P. | 0.002 mg |

The ingredients were blended to uniformity and compressed into a tablet for oral administration. One to four tablets are administered daily for treatment of viral infections.

EXAMPLE 112

An aerosol is prepared as follows:

Compound of Example 4 100 mg

Propylene glycol 20 mg

Dichlorotetrafluoroethane 600 mg (Propellant 14)

Dichlorodifluoromethane 500 mg (Propellant 12)

The components are mixed at −20° C. and placed into a sealed can equipped with a metering device.

EXAMPLE 113

A solution is prepared as follows:

Compound of Example 6 5 mg

Water 1 L

1N HCl 20 mL

The ingredients are mixed to form a solution which can be utilized to wash shower stalls in order to prevent and eliminate bacterial growth.

A further embodiment of this invention is a method of treating, preventing, and combatting viral infections. The method comprises administering an antivirally effective amount of a compound of this invention to a subject or surface in need of treatment. For example, the compounds of Formula I can be applied to shower stalls and public places in order to prevent, control, and combat vital growth. The compounds can be administered to animals, especially humans, to treat and prevent viral infections. As noted above, an effective amount of the active compound generally is about 5 to about 1000 mg per dosage unit, and ideally about 25 to about 750 mg.

The active ingredients of the therapeutic compositions and the compounds of the present invention exhibit excellent anti-retrovirus activity when administered in amounts ranging from about 1.0 to about 100 mg/kg of body weight per day. A preferred dosage regimen for optimum results would be from about 2.0 to about 50 mg/kg of body weight per day, and such dosage units are employed so that a total of from about 0.2 to about 3.0 g of the active compound for a subject of about 70 kg of body weight are administered in a 24-hour period. This dosage regimen may be adjusted to provide the optimum therapeutic response and is preferably administered one to four times a day in dosages of about 250 to about 750 mg per administration. For example, several divided doses may be administered daily or the dose may be proportionally reduced as indicated by the exigencies of the therapeutic situation. A decided practical advantage is that the active compound may be administered in a convenient manner such as by the oral, intravenous (where water soluble), intramuscular or subcutaneous routes.

The active compounds can be formulated as aqueous solutions and suspensions for washing surfaces such as wood, steel, ceramic, and the like in order to eliminate and control growth due to viruses.

Another embodiment of the invention is a method for treating atherosclerosis in mammals suffering therefrom and in need of treatment. The compounds are effective in inhibiting the activity of 15-lipoxygenase, and as such can be administered to a mammal, including a human, to effectively diminish and treat atherosclerosis. The compounds will be administered at a dose which is effective to treat atherosclerosis, typically from about 1.0 to about 100 mg/kg of body weight of the subject being treated.

The compounds also are useful for treating inflammation, for example, swelling due to injuries, swelling around bones and joints, and the like. The compounds will be administered to an animal suffering from inflammation in an amount that is effective to treat the inflammation. Typical doses will be from about 1.0 to about 100 mg/kg of body weight.

We claim:

1. A method for treating atherosclerosis comprising administering to a subject in need of treatment an amount effective to treat atherosclerosis of a compound of Formula I

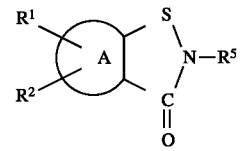

wherein:

A is a monocyclic ring having 5 or 6 ring atoms, or a bicyclic ring having from 9 to 12 ring atoms, the ring atoms being selected from carbon and optionally up to 3 heteroatoms selected from O, S, and N;

$R^1$ and $R^2$ independently are hydrogen, halo, $C_1$–$C_6$ alkyl, $C_3$–$C_6$ cycloalkyl, Het$(CR^6R^7)_m$—, phenyl-$(CR^6R^7)_m$—, O—$C_1$–$C_6$ alkyl, hydroxy, nitro, cyano, $NR^3R^4$, $NR^3COR^4$, $CO_2R^3$, $CONR^3R^4$, $S(O)_mR^3$, $SO_3H$, $S(O)_m NR^3R^4$, $COR^3$, or taken together are oxo (O=) or methylene dioxy (—O—$CH_2$—O—);

m is 0, 1, or 2;

R³ and R⁴ independently are hydrogen, $C_1-C_6$ alkyl, $C_3-C_6$ cycloalkyl, Het(CR⁶R⁷)$_m$—, or phenyl-(CR⁶R⁷)$_m$—;

R⁶ and R⁷ independently are hydrogen, $C_1-C_6$ alkyl, CO₂R³, hydroxy, CONR³R⁴, or cyano;

R⁵ is hydrogen, $C_1-C_6$ alkyl, COC$_1$-C$_6$ alkyl, $C_3-C_6$ cycloalkyl, phenyl-(CR⁶R⁷)$_m$—, Het(CR⁶R⁷)$_m$—; and wherein the foregoing alkyl, cycloalkyl, phenyl, and Het groups may optionally be substituted with from 1 to 3 groups selected from halo, hydroxy, nitro, NR³R⁴, NR³COR⁴, CO₂R³, CONR³R⁴, S(O)$_m$R³, S(O)$_m$NR³R⁴, and COR³, where m, R³, and R⁴ are as defined above;

and the pharmaceutically acceptable salts and solvates thereof.

2. A method of claim 1 employing a compound wherein A is a monocyclic ring having 6-ring atoms, one or two of which are heteroatoms selected from O, S, and N.

3. A method of claim 1 employing a compound of the formula

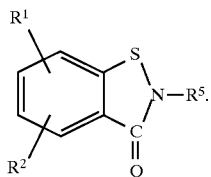

4. A method of claim 2 employing a compound of the formula

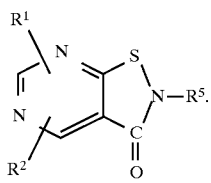

5. A method of claim 4 employing a compound wherein R⁵ is $C_1-C_6$ alkyl, phenyl-(CR⁶R⁷)$_m$—, or Het (CR⁶R⁷)$_m$—.

6. A method of claim 2 employing a compound of the formula

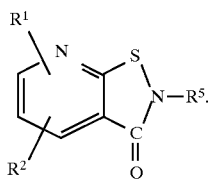

7. A method of claim 6 employing a compound wherein R⁵ is $C_1-C_6$ alkyl, phenyl-(CR⁶R⁷)$_m$—, or Het (CR⁶R⁷)$_m$—.

8. A method for treating inflammation comprising administering to a subject in need of treatment an anti-inflammatory effective amount of a compound of Formula I

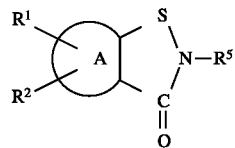

wherein:

A is a monocyclic ring having 5 or 6 ring atoms, or a bicyclic ring having from 9 to 12 ring atoms, the ring atoms being selected from carbon and optionally up to 3 heteroatoms selected from O, S, and N;

R¹ and R² independently are hydrogen, halo, $C_1-C_6$ alkyl, $C_3-C_6$ cycloalkyl, Het(CR⁶R⁷)$_m$—, phenyl-(CR⁶R⁷)$_m$—, O—$C_1-C_6$ alkyl, hydroxy, nitro, cyano, NR³R⁴, NR³COR⁴, CO₂R³, CONR³R⁴, S(O)$_m$R³, SO₃H, S(O)$_m$ NR³R⁴, COR³, or taken together are oxo (O=) or methylene dioxy (—O—CH₂—O—);

m is 0, 1, or 2;

R³ and R⁴ independently are hydrogen, $C_1-C_6$ alkyl, $C_3-C_6$ cycloalkyl, Het(CR⁶R⁷)$_m$—, or phenyl-(CR⁶R⁷)$_m$—;

R⁶ and R⁷ independently are hydrogen, $C_1-C_6$ alkyl, CO₂R³, hydroxy, CONR³R⁴, or cyano;

R⁵ is hydrogen, $C_1-C_6$ alkyl, COC$_1$-C$_6$ alkyl, $C_3-C_6$ cycloalkyl, phenyl-(CR⁶R⁷)$_m$—, Het (CR⁶R⁷)$_m$—; and wherein the foregoing alkyl, cycloalkyl, phenyl, and Het groups may optionally be substituted with from 1 to 3 groups selected from halo, hydroxy, nitro, NR³R⁴, NR³COR⁴, CO₂R³, CONR³R⁴, S(O)$_m$R³, S(O)$_m$NR³R⁴, and COR³, where m, R³, and R⁴ are as defined above;

and the pharmaceutically acceptable salts and solvates thereof.

9. A method of claim 8 employing a compound wherein A is a monocyclic ring having 6-ring atoms, one or two of which are heteroatoms selected from O, S, and N.

10. A method of claim 8 employing a compound having the formula

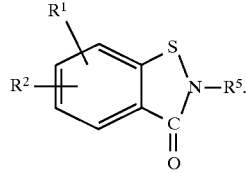

11. A method of claim 9 employing a compound of the formula

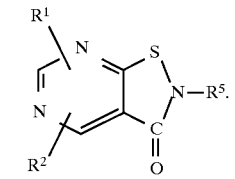

12. A method of claim 11 employing a compound wherein R⁵ is $C_1-C_6$ alkyl, Het(CR⁶R⁷)$_m$—, or phenyl-(CR⁶R⁷)$_m$—.

13. A method of claim 9 employing a compound of the formula

51
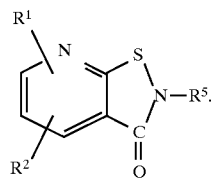
52
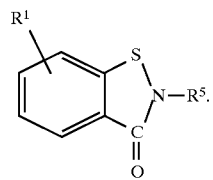
14. A method of claim 13 employing a compound wherein $R^5$ is $C_1$–$C_6$ alkyl, phenyl-$(CR^6R^7)_m$—, or Het$(CR^6R^7)_m$—.
15. A method of claim 8 employing a compound of the formula
16. A method of claim 15 employing a compound wherein $R^5$ is $C_1$–$C_6$ alkyl, phenyl-$(CR^6R^7)_m$—, Het$(CR^6R^7)_m$—.
* * * * *